US010294492B2

(12) United States Patent
Ramírez Martínez et al.

(10) Patent No.: US 10,294,492 B2
(45) Date of Patent: May 21, 2019

(54) STABLE EPISOMES BASED ON NON-INTEGRATIVE LENTIVIRAL VECTORS

(71) Applicant: Fundación Centro Nacional de Investigaciones Cariovasculares Carlos III (CNIC), Madrid (ES)

(72) Inventors: Juan Carlos Ramírez Martínez, Madrid (ES); Raúl Torres Ruiz, Madrid (ES); Aida García Torralba, Madrid (ES)

(73) Assignee: FUNDACIÓN CENTRO NACIONAL DE INVESTIGACIONES CARIOVASCULARES CARLOS III (CNIC), Madrid (ES)

( * ) Notice: Subject to any disclaimer, the term of this patent is extended or adjusted under 35 U.S.C. 154(b) by 0 days.

(21) Appl. No.: 15/100,110

(22) PCT Filed: Nov. 27, 2014

(86) PCT No.: PCT/EP2014/075869
§ 371 (c)(1),
(2) Date: May 27, 2016

(87) PCT Pub. No.: WO2015/078999
PCT Pub. Date: Jun. 4, 2015

(65) Prior Publication Data
US 2017/0022519 A1    Jan. 26, 2017

(30) Foreign Application Priority Data
Nov. 28, 2013    (EP) ..................................... 13382481

(51) Int. Cl.
C12N 15/86    (2006.01)
C12N 7/00    (2006.01)

(52) U.S. Cl.
CPC ............... *C12N 15/86* (2013.01); *C12N 7/00* (2013.01); *C12N 2740/10043* (2013.01); *C12N 2740/15043* (2013.01); *C12N 2820/80* (2013.01); *C12N 2820/85* (2013.01); *C12N 2830/46* (2013.01)

(58) Field of Classification Search
None
See application file for complete search history.

(56) References Cited

FOREIGN PATENT DOCUMENTS

| EP | 2020444 A1 * | 5/2007 | ............ A61K 39/00 |
|---|---|---|---|
| EP | 2 020 444 A1 | 2/2009 | |
| EP | 2020444 * | 2/2009 | ........... C12N 15/867 |

(Continued)

OTHER PUBLICATIONS

Aladjem et al., Science, 1995, 270: 815-819.
(Continued)

*Primary Examiner* — Janet L Andres
*Assistant Examiner* — Stuart W Snyder
(74) *Attorney, Agent, or Firm* — Jenkins, Wilson, Taylor & Hunt, P.A.

(57) ABSTRACT

The invention relates to non-integrative lentiviral vectors and their use for the stable transgenesis of both dividing and no-dividing eukaryotic cells. The invention also provides methods for obtaining these vectors, the use of these vectors for the production of recombinant lentiviruses, and the use of these recombinant lentiviruses for obtaining a cell able to stably produce a product of interest.

20 Claims, 10 Drawing Sheets
Specification includes a Sequence Listing.

(56) References Cited

FOREIGN PATENT DOCUMENTS

| | | |
|---|---|---|
| EP | 2 385 107 A1 | 11/2011 |
| WO | WO 96/01313 | 1/1996 |
| WO | WO 1997/038087 | 10/1997 |
| WO | WO 2000/006205 | 2/2000 |
| WO | WO 2000/063410 | 10/2000 |
| WO | WO 2001/081553 | 11/2001 |
| WO | WO 2005/112541 | 12/2005 |
| WO | WO 2008/065225 | 6/2008 |
| WO | WO 2010/105251 A2 | 9/2010 |
| WO | WO 2010/135401 A2 | 11/2010 |
| WO | WO 2013/153361 A1 | 10/2013 |

OTHER PUBLICATIONS

Altschul et al. Basic Local Alignment Search Tool. J Mol. Biol., Oct. 5, 1990, 215:403-10.
Araujo et al., J. Biol. Chem., 1999, 274(14): 9335-9341.
Benham et al., J. Mol. Biol., 1997, 274, 181-196.
Bethke & Sauer, Nucleic Acids Res., 1997, 25:2828-2834.
Bode et al., Science, 1992, 255: 195-7.
Bode et al., J. Mol. Biol. 2006, 358:597-613.
Buceta et al., "Use of human MAR elements to improve retroviral vector production," Gene Therapy, 2010, 18(1), 7-13.
Butler et al., J. Virol., 2002, 76(8): 3739. DOI: 10.1128/JVI.76.8.3739-3747.2002.
Cockerill & Garrard, Cell, 1986, 44(2): 273-282).
Frappier et al., Proc. Natl. Acad. Sci. USA, 1987, 84: 6668-72.
Grandchamp et al., "Influence of insulators on transgene expression from integrating and non-integrating lentiviral vectors," Genetic Vaccines and Therapy, 2011, 9(1), 1.
Kammler et al., Retrovirology, 2006, 3:89.
Kitsberg et al., Nature, 1993, 366(6455): 588-590.
Kramer et al., Genomics, 1996, 33, 305.
Kymäläinen, H.E., et al., "Long-term episomal transgene expression from mitotically stable integration-deficient lentiviral vectors (IDLVs)," Human Gene Therapy, Feb. 2, 2014; DOI: 10.1089/hum.2013.172.
Lefkowitz et al., Virology, 1990, 178(2):373-383.
McWhinney & Leffak, Nucleic Acids Res. 1990, 18(5): 1233-1242.
Mesner et al., Proc. Natl. Acad. Sci. U.S.A., 2003, 100(6): 3281-3286.
Nehlsen et al., Gene Therapy and Molecular Biology, 2006, 10: 233.
Pearson et al., Somat. Cell Mol. Genet. 1994, 20:147-152.
Price et al., Journal of Biological Chemistry, 2003, 278 (22): 19649-59.
Ramezani A. et al., Blood, 2003, 101(12): 4717-4724.
Singh et al., Nucl. Acids Res, 1997, 25, 1419.
Verghese et al., "S/MAR sequence confers long-term mitotic stability on non-integrating lentiviral vector episomes without selection," Nucleic Acids Research, Jan. 27, 2014. DOI: 10.1093/nar/gku082.
Yáñez-Muñoz et al., "Effective gene therapy with non-integrating lentiviral vectors," Nat. Med., 2006, 12(3): 348-353.
Yue et al., Hum Gene Ther., 2010, 21(6): 728-38.
Zabala et al. Cancer Res., 2004, 64:2799-2804.
Zufferey et al., Journal of Virology, 1998, 72: 9873-80.
Chen et al. (2017) Episomal lentiviral vectors confer erythropoietin expression in dividing cells. Plasmid. doi: 10.1016/j.plasmid.2017.02.001.
Haase et al. (2010) pEPito significantly improved non-viral episomal expression vector for mammalian cells. BMC Biotechnology. 10:20.
Haase et al. (2013) Generation of a tumor- and tissue-specific episomal non-viral vector system. BMC Biotechnology. 13:49.
Hagedorn et al. (2017) Genome-wide profiling of S/MAR-based replicon contact sites. Nucleic Acids Research. doi: 10.1093/nar/gkx522.
Hagedorn et al. (2017) S/MAR element facilitates episomal long-term persistence of Adeno-associated viral (AAV) vector genomes in proliferating cells.. Human Gene Therapy. doi: 10.1089/hum.2017.025.
Jin et al. (2016) Safe engineering of CAR T cells for adoptive cell therapy of cancer using long-term episomal gene transfer. EMBO Molecular Medicine. doi: 10.15252/emmm.201505869.
Stavrou et al. (2017) The β-globin Replicator greatly enhances the potential of S/MAR based episomal vectors for gene transfer into human haematopoietic progenitor cells. Scientific reports. 7:40673. DOI: 10.1038/srep40673.
Torres (2012) Diseño y desarrollo funcional de modelos vectoriales derivados de lentivirus deficientes en integración para la modificación génica específica de sitio. Universidad Autónoma de Madrid Facultad de Ciencias Departamento de Biología Molecular (full document in Spanish with abstract in English).
Vargas et al. (2008) Conditionally replicating lentiviral-hybrid episomal vectors for suicide gene therapy. Antiviral Res. 80:288-294. (Abstract).
Verghese et al. (2012) 4224 Episomal Anchorage Maintains Non-Integrating Lentiviral Vectors in Dividing Cells. 54th American Society of Hematology Annual Meeting and Exposition. (Abstract).
Xu et al. (2016) Non-integrating lentiviral vectors based on the minimal S/MAR sequence retain transgene expression in dividing cells. Science China Life Sciences. doi: 10.1007/s11427-016-0067-0.

* cited by examiner

A

B

STABLE EPISOMES BASED ON NON-INTEGRATIVE LENTIVIRAL VECTORS

FIELD OF THE INVENTION

The present invention falls within the field of eukaryotic cell transgenesis and, more specifically, relates to episomes based on non-integrative lentiviral vectors and their use for the generation of cell lines that stably express a heterologous gene of interest.

BACKGROUND OF THE INVENTION

Integrase deficient lentiviruses (IDLV) are non-replicative lentiviruses containing mutations in the catalytic domain of the viral integrase. As a consequence, circular cDNA off-products of the retrotranscription named 1-LTR and 2-LTR accumulate in the cell nucleus but are not able to integrate into the host genome (FIG. 1) (Yáñez-Muñoz R J et al., Nat. Med. 2006, 12: 348-353). As any other exogenous DNA those intermediates can integrate in the cellular DNA at equal frequencies (among $10^3$ to $10^5$/cell).

The extrachromosomal (episomal) properties of the IDLV-derived cDNAs has been avoids some of the disadvantages of classical lentiviruses. Episomal vectors display minimal interference with the cellular genome, thus minimizing both the position dependent expression profile of the transgenes delivered by the virus and the potential damage due to insertional mutagenesis. Despite the early enthusiasm captured for these novel vectors, a major concern is derived from their inability to replicate autonomously. Then the successive cell divisions lead the extinction of the lentivector sequences by the dilution of cells bearing the episomes, limiting their applicability to a narrow set of tissues and cells with low to null mitotic activity, as the nervous system. It follows that gene therapies based on these vectors are restricted to target senescent tissues or cells with very low rate of cell divisions to ensure permanence of the corrected phenotype driven by the transgene. Unfortunately many potentially treatable diseases by gene therapy rely on modify highly dividing cells or tissues undergoing life-spanning cell divisions like hematopoietic or epithelial stem cells as well as stem/iPS cells-based cures that are not target of these vectors.

SUMMARY OF THE INVENTION

In a first aspect, the invention relates to a polynucleotide comprising
(i) a first long terminal repeat derived from a lentivirus,
(ii) an eukaryotic origin of replication selected from the group consisting of the origins of replication having the sequence of SEQ ID NO: 1, SEQ ID NO: 2, SEQ ID NO: 3 and a functionally equivalent variant thereof,
(iii) a scaffold/matrix attachment region selected from the group consisting of the scaffold/matrix attachment regions having the sequence of SEQ ID NO: 4, SEQ ID NO: 5, SEQ ID NO: 6 and a functionally equivalent variant thereof, and
(iv) a second long terminal repeat derived from said lentivirus,
wherein said eukaryotic origin of replication and said scaffold/matrix attachment region are located between said first and second long terminal repeats.

In a second aspect, the invention relates to a vector comprising the polynucleotide according to the first aspect.

In a third aspect, the invention relates to a cell comprising the polynucleotide according to the first aspect or the vector according to the second aspect.

In a fourth aspect, the invention relates to a recombinant lentivirus comprising a polynucleotide according to the first aspect and a lentiviral integrase comprising a mutation that causes said integrase to be unable to catalyze the integration of the viral genome into a cell genome.

In a fifth aspect, the invention relates to an in vitro method for generating a recombinant lentivirus according to the fourth aspect comprising
  (i) contacting an eukaryotic cell with a polynucleotide according to the first aspect or with a vector according to the second aspect, wherein the cell expresses the products of the lentiviral genes gag, pol, rev and a viral envelope protein under conditions adequate for entry of the polynucleotide or vector in said cell and
  (ii) maintaining the cell under conditions adequate for assembly of the lentivirus.

In a sixth aspect, the invention relates to a stable cell population which can express a polynucleotide of interest comprising the polynucleotide according to the first aspect wherein said polynucleotide comprises the sequence of a polynucleotide of interest operatively linked to a promoter wherein
  the promoter is located at a 5' position with respect to the scaffold/matrix attachment region and with respect to the origin of replication and at a 3' position with respect to the first long terminal repeat and
  the polynucleotide of interest is located at a 5' position or at a 3' position with respect to the scaffold/matrix attachment region and at a 5' position or at a 3' position with respect to the origin of replication.

In a seventh aspect, the invention relates to an in vitro method for generating the stable cell population of the sixth aspect comprising the steps of
  (i) contacting cells with the recombinant lentivirus according to the fourth aspect, wherein the recombinant lentivirus comprises the sequence of a polynucleotide of interest operatively linked to a promoter wherein
    the promoter is located at a 5' position with respect to the scaffold/matrix attachment region and with respect to the origin of replication and at a 3' position with respect to the first long terminal repeat and
    the polynucleotide of interest is located at a 5' position or at a 3' position with respect to the scaffold/matrix attachment region and at a 5' position or at a 3' position with respect to the origin of replication, and
  (ii) growing and maintaining the cells.

In an eighth aspect, the invention relates to a use of the stable cell population according to the sixth aspect for the in vitro production of a product of interest.

In a ninth aspect, the invention relates to an in vitro method for the production of a product of interest comprising culturing a stable cell population according to the sixth aspect under conditions allowing the expression of the polynucleotide of interest.

DETAILED DESCRIPTION OF THE INVENTION

Figure 1:
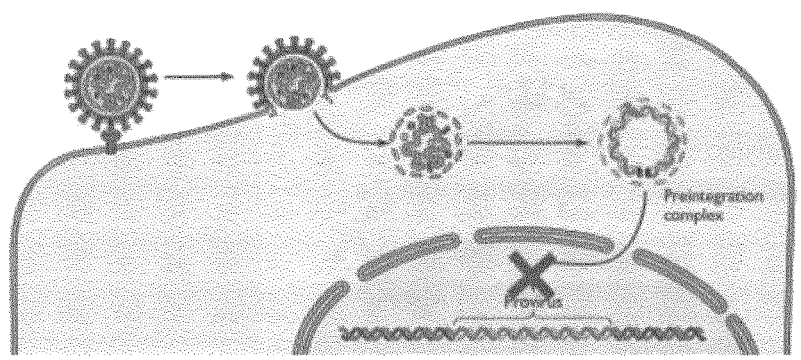
FIG. 1. Schematic representation of relevant steps in lentiviral cycle. (Upper) The early steps in lentivirus infection are shown (entry, desencapsidation and retrotranscription). The inhibition of retrotranscription is remarked by a crossed indicative of the IDLV restrictions. (Bottom) On the right are shown schematically linear, 1-LTR and 2-LTR of-products of the retrotranscription. The two latter are no common substrates for integration by the viral enzyme but are generated by NHEJ and HR respectively.
Figure 1:
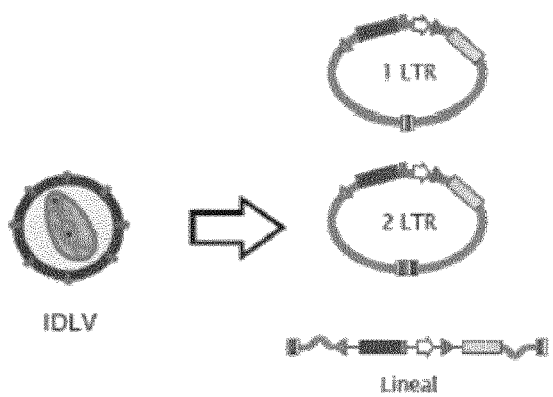

The inventors of the present invention have developed a system for the stable transgenesis of eukaryotic cells based on lentiviral vectors carrying a mutation that prevents the integrase-mediated integration into the cell genome by incorporating into these vectors an eukaryotic origin of replication and a scaffold/matrix attachment region (S/MAR) for association with the nuclear matrix. By incorporating these elements into vectors, the authors of the present invention have made lentiviral episomes able to replicate and segregate into daughter cells, thereby achieving stable expression of the transgene both in quiescent cells and actively dividing cells without the intervention of viral proteins (see FIG. 4 and table 1). This strategy results in an expression system with higher biosafety compared to similar systems of the prior art.

The co-transfection of a packaging cell line with the lentiviral vector designed by the inventors in the presence of the proteins necessary for packaging of the vector into infectious non-integrative lentiviral particles allows the production of a new type of non-integrative lentivirus suitable for stable expression of a transgene in a target cell.

Moreover, the inventors have observed that not all the combinations of well-known eukaryotic origins of replication and S/MAR are equally efficient for the stably establishment of lentiviral episomes. Thus, some of the combinations give rise to lentiviruses which are not able to generate a significant stable expression of the gene of interest (see LS 4, 8 and 12 in FIG. 4).

Based on the previous findings, the following inventive aspects have been developed.

Polynucleotide of the Invention

In a first aspect, the invention relates to a polynucleotide, hereinafter polynucleotide of the invention, comprising
(i) a first long terminal repeat derived from a lentivirus,
(ii) an eukaryotic origin of replication selected from the group consisting of the origins of replication having the sequence of SEQ ID NO: 1, SEQ ID NO: 2, SEQ ID NO: 3 and a functionally equivalent variant thereof,
(iii) a scaffold/matrix attachment region selected from the group consisting of the scaffold/matrix attachment regions having the sequence of SEQ ID NO: 4, SEQ ID NO: 5, SEQ ID NO: 6 and a functionally equivalent variant thereof, and
(iv) a second long terminal repeat derived from said lentivirus,
wherein said eukaryotic origin of replication and said scaffold/matrix attachment region are located between said first and second long terminal repeats.

The term "polynucleotide", as used herein, refers to a single or double stranded polymer of deoxyribonucleotide or ribonucleotide bases.

First Long Terminal Repeat

The first element of the polynucleotide of the invention is a first long terminal repeat. During the natural course of reverse transcription, sequences from the 5' (R-U5) and 3' (U3-R) ends of retroviral genomic RNA are fused through the direct repeat sequence R, and duplicated to form a linear duplex molecule with long terminal repeats. Subsequent insertion of this molecule into a site within the chromosomal DNA of an infected host cell allows the viral DNA to function as a template for the transcription of new viral RNA molecules.

The term "long terminal repeat" or "LTR", as used herein, refers to a sequence of several hundred base pairs at each end of the DNA synthesized by the reverse transcription of retroviral RNA that controls integration of the viral DNA into the host DNA and the expression of the genes of the virus. As used herein, the LTR refers to both the DNA sequence of the LTR as found in the DNA synthesized by the reverse transcription of the retroviral RNA and to the RNA sequence which is complementary to said DNA sequence of the LTR. The 5' LTR and 3' LTR serve to promote transcription and polyadenylation of the RNA of the virus. The LTR contains all other cis-acting sequences necessary for viral replication. Each LTR comprises a U3, R and U5 region.

The term "first long terminal repeat" or "first LTR" or "5' LTR" refers to a 5' lentiviral LTR, which may or may not be modified from its corresponding native 5' LTR by deleting and/or mutating endogenous sequences and/or adding heterologous sequences. The 5' LTR may be natural or synthetic.

Both the first and second LTR of the polynucleotide of the invention derive from a lentivirus. The term "lentivirus", as used herein, refers to a group (or scientific genus) of retroviruses that in nature give rise to slowly developing disease due to their ability to incorporate into a host genome. These viruses include in particular Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV). In a preferred embodiment, the lentivirus is HIV. Thus, in a particular embodiment, the first and second LTR derive form HIV.

The term "human immunodeficiency virus" or "HIV", as used herein, is meant to include HIV-1 and HIV-2. "HIV-1" means the human immunodeficiency virus type-1. HIV-1 includes, but is not limited to, extracellular virus particles and HIV-1 forms associated with HIV-1 infected cells. "HIV-2" means the human immunodeficiency virus type-2. HIV-2 includes, but is not limited to, extracellular virus particles and HIV-2 forms associated with HIV-2 infected cells. Preferably, HIV is HIV-1.

In a preferred embodiment, the first LTR of the polynucleotide of the invention comprises the sequence shown in SEQ ID NO: 7. In a particular embodiment, the first LTR of the polynucleotide of the invention consists on the sequence shown in SEQ ID NO: 7.

Eukaryotic Origin of Replication

The polynucleotide of the invention comprises a eukaryotic origin of replication. The terms "eukaryotic origin of replication" or "eukaryotic replication origin" or "eukaryotic ori", as used herein, refer to a particular genome sequence at which the replication is initiated in eukaryotes. The term "eukaryote", as used herein, comprises the kingdoms Protista, Fungi, Plantae and Animalia.

The eukaryotic origin of replication that is part of the polynucleotide of the invention is selected from the group consisting of the origins of replication having the SEQ ID NO: 1, SEQ ID NO: 2, SEQ ID NO: 3 and a functionally equivalent variant thereof.

The origin of replication having the sequence of SEQ ID NO: 1 corresponds to the origin of replication of the β-globin gene as have been described by Aladjem et al (Science, 1995, 270: 815-819).

The origin of replication having the sequence of SEQ ID NO: 2 derives from a consensus sequence from autonomously replicating sequences associated with alpha-satellite sequences isolated previously from monkey CV-1 cells and human skin fibroblasts as has been described by Price et al Journal of Biological Chemistry, 2003, 278 (22): 19649-59.

The origin of replication having the sequence of SEQ ID NO: 3 corresponds to the origin of replication of the human c-myc promoter region has have been described by McWinney and Leffak (McWinney C. and Leffak M., Nucleic Acid Research 1990, 18(5): 1233-42).

In a particular embodiment, the polynucleotide of the invention comprises the origin of replication having the sequence SEQ ID NO: 1 or a functionally equivalent variant thereof.

In a particular embodiment, the polynucleotide of the invention comprises the origin of replication having the sequence SEQ ID NO: 2 or a functionally equivalent variant thereof.

In a particular embodiment, the polynucleotide of the invention comprises the origin of replication having the sequence SEQ ID NO: 3 or a functionally equivalent variant thereof.

The term "functionally equivalent variant", as used herein, refers to a variant of any of the origins of replication of sequence SEQ ID NO: 1, SEQ ID NO: 2 or SEQ ID NO: 3 that is substantially identical and performs substantially the same function as the sequence from which it derives. As used herein, "substantially identical" means that the nucleic acid sequence has a degree of sequence identity of at least a 50%, at least a 55%, at least a 60%, at least a 65%, at least 70%, at least a 75%, at least a 80%, at least a 85%, at least a 90%, at least a 95%, at least a 96%, at least a 97%, at least 98% or at least 99% with the sequence from which it is derived. The degree of sequence identity between two polynucleotides can be determined by conventional methods, for example, by standard alignment algorithms known in the art such as, for example BLAST Altschul S. F. et al. Basic Local Alignment Search Tool. J Mol. Biol. 1990 Oct. 5; 215:403-10). In a preferred embodiment, the degree of sequence identity is determined across the whole length of the polynucleotides.

In a preferred embodiment, the variant of the origin of replication having the sequence SEQ ID NO: 2 comprises the following consensus sequence (SEQ ID NO: 25)
CCTMDAWKSGBYTSMAAWTWBCMYTTRSCAAATTCC wherein M is A or C; D is A, G or T; W is A or T; K is G or T; S is C or G; B is C, G or T; Y is C or T; R is A or G and H is A, C or T.

In another embodiment, the variant of the origin of replication having the sequence SEQ ID NO: 2 comprises a sequence selected from the group consisting of A6, A7, A15, A16, A1, A5 and A39 as shown in Table I in Price et al. (J. Biol. Chem., 2003, 278:19649-19659).

The term "substantially the same function", as used herein, means that the variant substantially maintains the ability to initiate the replication in eukaryotes. The skilled person knows how to determine if a particular variant is able to initiate the replication in eukaryotes and, therefore, if it is functionally equivalent to the origins of replication of SEQ ID NO: 1, SEQ ID NO: 2 or SEQ ID NO: 3. The ability of a particular sequence of initiating replication can be determined by any suitable method known by the skilled person, for example, resistance to digestion by DpnI (Frappier L. et al., Proc. Natl. Acad. Sci. USA, 1987, 84: 6668-72), by the earliest labeled fragment assay (Pearson et al, Somat. Cell Mol. Genet. 1994, 20:147-152) and the autonomous replication assay based on bromodeoxyuridine incorporation and density shift (Araujo F. D. et al., supra; Frappier L. et al., supra).

Scaffold/Matrix Attachment Region

The polynucleotide of the invention comprises a scaffold/matrix attachment region. The term "scaffold/matrix attachment region" or "S/MAR", as used herein, refers to non-consensus-like AT-rich DNA elements several hundred base pairs in length, which organize the nuclear DNA of the eukaryotic genome into some 60,000 chromatin domains, by periodic attachment to the protein scaffold or matrix of the cell nucleus. They are typically found in non-coding regions such as flanking regions, chromatin border regions, and introns.

The S/MAR forming part of the polynucleotide of the invention is selected from the group consisting of the S/MAR having the sequence of SEQ ID NO: 4, SEQ ID NO: 5, SEQ ID NO: 6 and a functionally equivalent variant thereof.

The S/MAR having the sequence of SEQ ID NO: 4 corresponds to the 1.8 kbp S/MAR of the human IFN-γ gene (hIFN-γ$^{large}$) has have been described by Bode et al (Bode J. et al., Science, 1992, 255: 195-7).

The S/MAR having the sequence of SEQ ID NO: 5 corresponds to the 0.7 Kbp minimal region of the S/MAR of the human IFN-γ gene (hIFN-γ$^{short}$) as has have been described by Ramezani (Ramezani A. et al., Blood 2003, 101: 4717-24).

The S/MAR having the sequence of SEQ ID NO: 6 corresponds to the 0.2 Kbp minimal region of the S/MAR of the human dehydrofolate reductase gene (hDHFR) as has been described by Mesner L. D. et al., Proc Natl Acad Sci USA, 2003, 100: 3281-86).

In a particular embodiment, the polynucleotide of the invention comprises the S/MAR having the sequence SEQ ID NO: 4 or a functionally equivalent variant thereof.

In a particular embodiment, the polynucleotide of the invention comprises the S/MAR having the sequence SEQ ID NO: 5 or a functionally equivalent variant thereof.

In a particular embodiment, the polynucleotide of the invention comprises the S/MAR having the sequence SEQ ID NO: 6 or a functionally equivalent variant thereof.

The term "functionally equivalent variant", as used herein, refers to a variant of any of the S/MAR of sequence SEQ ID NO: 4, SEQ ID NO: 5 or SEQ ID NO: 6 that is substantially homologous and performs substantially the same function as the S/MAR from which it derives. As used herein, "substantially homologous" means that the nucleic acid sequence has a degree of sequence identity of least a 50%, at least a 55%, at least a 60%, at least a 65%, at least 70%, at least a 75%, at least a 80%, at least a 85%, at least a 90%, at least a 95%, at least a 96%, at least a 97%, at least 98% or at least 99% with the sequence from which it is derived.

In a preferred embodiment, the functionally equivalent variant of the S/MAR is a sequence selected based on the set six rules that together or alone have been suggested to contribute to S/MAR function (Kramer et al (1996) *Genomics* 33, 305; Singh et al (1997) *Nucl. Acids Res* 25, 1419). These rules have been merged into the MAR-Wiz computer program freely available at http://genomecluster.secs.oakland.edu/MAR-Wiz.

The term "substantially the same function", as used herein, means that the variant substantially maintains the same functions of the S/MAR from which it derives, in particular, the ability to specifically bind to the nuclear matrix. The skilled person knows how to determine if a particular variant is able to specifically bind to the nuclear matrix, for example by the in vitro or in vivo MAR assays described by Mesner et al. (Mesner L. D. et al, supra). In another embodiment, a specific sequence can be considered as a variant of a S/MAR according to the present invention if the particular variant shows propensity for DNA strand separation. This property can be determined using a specific program based on methods from equilibrium statistical mechanics. The stress-induced duplex destabilization (SIDD) analysis technique "[ . . . ] calculates the extent to which the imposed level of superhelical stress decreases the free energy needed to open the duplex at each position along a DNA sequence. The results are displayed as an SIDD profile, in which sites of strong destabilization appear as deep minima [ . . . ]" as defined in Bode et al (2005) *J. Mol. Biol.* 358,597. Data obtained from SIDD analysis (minim in the output representation) have been experimentally corroborated with experimentally determined base unpairing regions or to correlate with functional roles of S/MAR likewise binding activity or plasmid vector retention. Overall these data suggest that the SIDD properties may be incorporate to into any computational strategy to search genomic sequences for sites having the features to function as S/MARs, although current available data is not supportive enough for estimate their relative binding strengths. The SIDD algorithm and the mathematical basis (Bi and Benham (2004) Bioinformatics 20, 1477) and the analysis of the SIDD profile can be performed using the freely available internet resource at WebSIDD (http://www.genomecenter.ucdavis.edu/benham). Accordingly, in another embodiment, the polynucleotide is considered a variant of the S/MAR sequence if it shows a similar SIDD profile as the S/MAR.

In a particular embodiment, the polynucleotide of the invention comprises the origin of replication having the sequence SEQ ID NO: 1 or a functionally equivalent variant thereof and the S/MAR having the sequence SEQ ID NO: 4 or a functionally equivalent variant thereof.

In a particular embodiment, the polynucleotide of the invention comprises the origin of replication having the sequence SEQ ID NO: 1 or a functionally equivalent variant thereof and the S/MAR having the sequence SEQ ID NO: 5 or a functionally equivalent variant thereof.

In a particular embodiment, the polynucleotide of the invention comprises the origin of replication having the sequence SEQ ID NO: 1 or a functionally equivalent variant thereof and the S/MAR having the sequence SEQ ID NO: 6 or a functionally equivalent variant thereof.

In a particular embodiment, the polynucleotide of the invention comprises the origin of replication having the sequence SEQ ID NO: 2 or a functionally equivalent variant thereof and the S/MAR having the sequence SEQ ID NO: 4 or a functionally equivalent variant thereof.

In a particular embodiment, the polynucleotide of the invention comprises the origin of replication having the sequence SEQ ID NO: 2 or a functionally equivalent variant thereof and the S/MAR having the sequence SEQ ID NO: 5 or a functionally equivalent variant thereof.

In a particular embodiment, the polynucleotide of the invention comprises the origin of replication having the sequence SEQ ID NO: 2 or a functionally equivalent variant thereof and the S/MAR having the sequence SEQ ID NO: 6 or a functionally equivalent variant thereof.

In a particular embodiment, the polynucleotide of the invention comprises the origin of replication having the sequence SEQ ID NO: 3 or a functionally equivalent variant thereof and the S/MAR having the sequence SEQ ID NO: 4 or a functionally equivalent variant thereof.

In a particular embodiment, the polynucleotide of the invention comprises the origin of replication having the sequence SEQ ID NO: 3 or a functionally equivalent variant thereof and the S/MAR having the sequence SEQ ID NO: 5 or a functionally equivalent variant thereof.

In a particular embodiment, the polynucleotide of the invention comprises the origin of replication having the sequence SEQ ID NO: 3 or a functionally equivalent variant thereof and the S/MAR having the sequence SEQ ID NO: 6 or a functionally equivalent variant thereof.

Certain S/MARs contain adenine-rich regions. The presence of adenine-rich regions in a polynucleotide is detrimental to the transcription of the polynucleotide (if the polynucleotide is DNA) or to the replication of the polynucleotide (if the polynucleotide is RNA) as it may lead to premature termination of the transcription/replication and to the generation of incomplete transcripts. Accordingly, since S/MARs are regions that can perform their activity in any orientation, i.e. they are reversible, the skilled person will understand that in those cases in which the S/MAR contains an adenine-rich region, the S/MAR is inserted into the polynucleotide of the invention with an orientation so that any adenine-rich region in one strand of the S/MAR does not negatively affect the transcription of the polynucleotide sequence. Accordingly, if the polynucleotide of the invention is a single-stranded DNA (ssDNA) or a single-stranded RNA (ssRNA), the polynucleotide comprises a sequence which is the reverse complement of the strand of the S/MAR that comprises the adenine rich region. If the polynucleotide of the invention is a double-stranded DNA (dsDNA), then the S/MAR is inserted into the polynucleotide so that the strand of the S/MAR that comprises the adenine-rich region does not form part of the coding strand of said dsDNA.

The terms "single-stranded DNA" or "ssDNA", as used herein, refer to a DNA polynucleotide comprising only one strand.

The terms "single-stranded RNA" or "ssRNA", as used herein, refer to a RNA polynucleotide comprising only one strand.

The terms "double-stranded DNA" or "dsDNA", as used herein, refer to a DNA polynucleotide comprising two antiparallel and substantially complementary DNA strands bonded by hydrogen bonds.

The term "adenine-rich region", as used herein, refers to a region in a polynucleotide wherein adenine is the most abundant nucleotide. In a preferred embodiment, the adenine-rich region is a polyadenine sequence. The term "polyadenine sequence" or "polyA sequence", as used herein, refer to a polynucleotide sequence comprising multiple consecutive adenosine monophosphates.

The term "coding strand", as used herein, refers to the DNA strand which is complementary to the template strand. Such coding strand has the same base sequence as the mRNA (although with thymine replaced by uracil) and corresponds to the codons that are translated into protein.

In a more particular embodiment, when the polynucleotide of the invention comprises the S/MAR having the sequence SEQ ID NO: 6 or a functionally equivalent variant thereof, if said polynucleotide is a ssDNA or a ssRNA, then said polynucleotide comprises a sequence which is the reverse complement to the strand of the S/MAR that comprises the polyA sequence.

In another more particular embodiment, when the polynucleotide of the invention comprises the S/MAR having the sequence SEQ ID NO: 6 or a functionally equivalent variant thereof, if said polynucleotide is a dsDNA, then the S/MAR is inserted into the polynucleotide so that the strand of the S/MAR that comprises the adenine-rich region does not form part of the coding strand of said dsDNA.

Second Long Terminal Repeat

The terms "second long terminal repeat" or "second LTR" or "3' LTR" refer to a 3' lentiviral LTR, which may or may not be modified from its corresponding native 3' LTR by deleting and/or mutating endogenous sequences and/or adding heterologous sequences. The 3' LTR may be natural or synthetic.

The second LTR of the polynucleotide of the invention derives from the same lentivirus as the first LTR. In a particular embodiment, the second LTR derives from HIV.

In a preferred embodiment, the second LTR comprises a self-inactivation mutation. The term "mutation", as used herein, refers to a change in a nucleic acid sequence. Said mutation include, but is not limited to, substitution (i.e. exchanging one or more nucleotides for others), inversion (i.e. a DNA segment inside a gene is inverted, to that end two 180° rotations are necessary, one for inverting the sequence and the other for maintaining the polarity of the DNA), translocation (i.e. a segment of a gene changes position to be in another different site of the same gene or in another site of the genome), and nucleotide insertions or deletions (i.e. the addition of one or more nucleotides (insertions or additions) or the loss of one or more nucleotides (deletions) having as a consequence changes in the reading frame, a reading error occurring during the translation ranging from the formation of non-functional proteins to the absence of said protein). The term "self-inactivating mutation", as used herein, refers to a mutation that causes that the LTR has a reduced ability to promote the transcription of a transcript compared with its corresponding native LTR. The ability of a LTR of promoting the transcription of a transcript can be determined by the skilled person by any technique suitable for analyzing the promoter activity of an LTR, for example, by determining the amount of RNA production derived from the LTR internal promoter with the assay described by Zufferey et al. (Zufferey et al., Journal of Virology, 1998, 72: 9873-80). The term "reduced ability to promote the transcription of a transcript" means any significant reduction in the promoter activity of the mutated LTR compared with its native counterpart, for example, a reduction of at least 10%, at least 20%, at least 30%, at least 40%, at least 50%, at least 60%, at least 70%, at least 80%, at least 90% or 100% in the promoter activity of the mutated LTR compared with its corresponding native LTR. Mutations in the LTR of lentiviruses useful for the generation of self-inactivating (SIN) lentiviral vectors are have been described in the art (Zufferey R et al., J. Virol. 1998, 72: 9873-9880).

In a preferred embodiment, when the polynucleotide of the invention is incorporated into a lentiviral vector, the self-inactivating mutation present on the second LTR does not affect to the transducing ability of said vector compared with an equivalent vector that comprises the corresponding native LTR, i.e. the ability of the vector to be transferred to a target cell remains essentially unaffected. The skilled person can determined the transduction ability of a lentiviral vector by any technique known in the art, for example, determining the vector titers in target cells by the method described by Zufferey et al. (Zufferey et al., supra).

In a particular embodiment, the mutation is a deletion.

In another particular embodiment, the mutation affects the U3 region of the LTR. The term "U3 region of the LTR", as used herein, refers to the region of the LTR that comprises enhancer and promoter elements. In the particular case of the HIV-1 LTR, the U3 region comprises all the major determinants responsible for regulating the HIV-1 LTR promoter activity, like the so-called negative response element, NFκB and NF-ATc binding sites, Sp1 binding sites and a TATA box.

In a preferred embodiment, the mutation is a deletion in the U3 region of the second LTR. Any deletion in the U3 region that is able to reduce the ability of the LTR of promoting the transcription of a transcript is suitable for the polynucleotide of the invention, for example, a deletion of the TATA box and/or a deletion of one or more of the binding sites for the transcription factors. In a more preferred embodiment, the deletion in the U3 region of the second LTR comprises the deletion of the sequence comprised between the −418 (5') and the −18 (3') positions, the numbering indicating the nucleotide positions relative to the cap site at the beginning of R, at position +1. In a particular embodiment, the second LTR comprising a deletion in the U3 region comprises the sequence SEQ ID NO: 8. In a more particular embodiment, the second LTR comprising a deletion in the U3 region consists on the sequence SEQ ID NO: 8.

In the polynucleotides of the invention, the eukaryotic origin of replication and the S/MAR are located between the first and second LTR. In a preferred embodiment, the origin of replication is located at a 5' position with respect to the S/MAR, being the order of elements of the polynucleotide from 5' to 3':
  first LTR
  origin of replication
  S/MAR
  second LTR In another particular embodiment, the S/MAR is located at a 5' position with respect to the origin of replication, being the order of elements of the polynucleotide from 5' to 3':
  first LTR
  S/MAR
  origin of replication
  second LTR In a particular embodiment, the polynucleotide of the invention further comprises a polynucleotide sequence selected from
  a multiple cloning site,
  a polynucleotide of interest operatively linked to a promoter wherein the promoter is located at a 5' position with respect to the scaffold/matrix attachment region and with respect to the origin of replication and at a 3' position with respect to the first long terminal repeat and
  the polynucleotide of interest is located at a 5' position or at a 3' position with respect to the scaffold/matrix attachment region and at a 5' position or at a 3' position with respect to the origin of replication and
  a combination thereof.

In a particular embodiment, the polynucleotide of the invention comprises a multiple cloning site. The term "multiple cloning site", as used herein, refers to a DNA fragment comprising several target sites for restriction endonucleases close to one another such that they cleave the polynucleotide in a single position. Thus, after the treatment of the polynucleotide with said endonucleases it is possible to insert a gene of interest having compatible ends, said ends being blunt, 5'-protruding or 3'-protruding ends. In principle, it is possible to use any multiple cloning site known in the art such as that which can be obtained from vectors of the type of pUC18, pUC19, etc. The insertion of polynucleotides of interest is carried out using standard molecular biology methods as described, for example, by Sambrook et al. (Molecular Cloning: A Laboratory Manual (1982); "*DNA Cloning: A Practical Approach*," Volumes 1 and II). The multiple cloning site preferably comprises at least 1, 2, 3, 4, 5, 6, 7, 8, 9 or 10 target sites for a restriction endonuclease, each of them formed by at least 4, at least 5 or at least 6 nucleotides.

In a particular embodiment, the polynucleotide of the invention comprises a polynucleotide of interest operatively linked to a promoter.

The term "promoter", as used herein, refers to a nucleic acid fragment that functions to control the transcription of one or more polynucleotides, located upstream the polynucleotide sequence(s), and which is structurally identified by the presence of a binding site for DNA-dependent RNA polymerase, transcription initiation sites, and any other DNA sequences including, but not limited to, transcription factor binding sites, repressor, and activator protein binding sites, and any other sequences of nucleotides known in the art to act directly or indirectly to regulate the amount of transcription from the promoter. Said promoter could be either constitutive or inducible. A "constitutive promoter" is a promoter that is active under most physiological and developmental conditions. An "inducible" promoter is a promoter that is regulated depending on physiological or developmental conditions. A "tissue specific" promoter is only active in specific types of differentiated cells/tissues. In a preferred embodiment, the promoter is a viral promoter, more preferably a promoter derived from an adeno-associated virus (AAV). The term "adeno-associated virus" or "AAV" refers to viruses belonging to the genus Dependovirus of the Parvoviridae family. In a more particular embodiment, the promoter derived from an AAV is the p5 promoter or a functionally equivalent variant thereof. The term "p5 promoter", as used herein, refers to the promoter of AAV that controls the expression of Rep68 and Rep 78 (Yue Y. B. et al., Hum Gene Ther 2010, 21(6): 728-38). In a more particular embodiment, the promoter derived from an AAV comprises the sequence of SEQ ID NO: 9. In an even more particular embodiment, the promoter derived from an AAV consists on the sequence of SEQ ID NO: 9. In a particular embodiment, the promoter is a functionally equivalent variant of the p5 promoter. The term "functionally equivalent variant", as used in the context of the p5 promoter, refers to a variant that is substantially homologous to the p5 promoter and performs substantially the same function. The term "substantially homologous" has been previously defined. A variant that performs substantially the same function as the p5 promoter is a variant that is able to control the expression of a polynucleotide of interest located downstream of said variant.

The term "operably linked", as used herein, refers to the functional relation and location of a promoter sequence with respect to a polynucleotide of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

When the polynucleotide of the invention comprises a polynucleotide of interest operatively linked to a promoter, the components of the polynucleotide have the following disposition:
  the promoter is located
    upstream the S/MAR and the origin of replication, i.e., at a 5' position with respect to the S/MAR and with respect to the origin of replication, and
    downstream the first LTR, i.e., at a 3' position with respect to the first LTR; and the polynucleotide of interest is located
    upstream or downstream the S/MAR, i.e., at a 5' position or at a 3' position with respect to the S/MAR and
    upstream or downstream the origin of replication, i.e., at a 5' position or at a 3' position with respect to the origin of replication.

In a particular embodiment, the polynucleotide of the invention comprising a polynucleotide of interest operatively linked to a promoter further comprises an enhancer region operatively linked to the promoter. The term "enhancer", as used herein, refers to a DNA sequence element to which transcription factors bind to increase gene transcription. In a more particular embodiment, the enhancer region is the enhancer region of the cytomegalovirus promoter. In an even more particular embodiment, the enhancer region of the cytomegalovirus promoter comprises the sequence SEQ ID NO: 10. In a still more particular embodiment, the enhancer region of the cytomegalovirus promoter consists on the sequence SEQ ID NO: 10.

The term "polynucleotide of interest", as used herein, refers to any polynucleotide whose expression in a cell is desirable. The polynucleotide of interest can be a gene encoding a polypeptide or protein or a polynucleotide that, once transcribed, generates an RNA which is able to hybridize with a mRNA inhibiting its expression like, for example, a microRNA, a siRNA or a shRNA. In a particular embodiment, the polynucleotide of interest is selected from a selection gene, a polynucleotide encoding a protein of interest and a combination thereof.

The term "selection gene", as used herein, refers to a gene whose expression confers resistance to an antibiotic, a gene that allows synthesizing an essential nutrient which is absent from the culture medium or a gene that provides a selective advantage to cells that have incorporated said selection gene.

In a preferred embodiment, the selection gene is a gene that encodes a protein conferring resistance to an antibiotic, for example, a gene that encodes a protein conferring resistance to hygromycin, a gene that encodes a protein conferring resistance to neomycin, a gene that encodes a protein conferring resistance to puromycin, etc. In a more preferred embodiment, the selection gene encodes a protein conferring resistance to neomycin.

Alternatively, the selection gene is a gene which allows synthesizing an essential nutrient which is absent in the culture medium. An example includes the trpB gene of *Escherichia coli*, which encodes the beta subunit of tryptophan synthase. This gene allows survival and proliferation of mammalian cells in medium containing indole instead of tryptophan. A second example includes the hisD gene of *Salmonella typhimurium*, which encodes histidinol dehydrogenase, which catalyzes the NAD-dependent oxidation of L-histidinol+L-histidine in two stages. Only mammalian cells expressing the product hisD can survive in medium lacking histidine and containing histidinol (Hartman S C and R C Mulligan, Proc. Natl. Acad Sci. USA. 1988, 85 (21): 8047-51).

An example of a selection gene providing a selective advantage to cells that have incorporated said gene includes the gene encoding dihydrofolate reductase (DHFR) in cells genetically engineered to be deficient in DHFR. DHFR protein catalyzes the reduction of 5,6-dihydrofolate to 5,6,7,8-tetrahydrofolate, an essential step in the purine metabolism. Using DHFR enables the genetic selection of DHFR-deficient cells by growing them in the absence of purine precursors hypoxanthine and thymidine (HT) (R J Kaufman and P A Sharp, J. Mol. Biol, 1982, 159: 601-21).

The term "protein of interest" as used herein, refers to any protein whose expression in a cell is desirable. In a particular embodiment, the protein of interest is a fluorescent protein, preferably the green fluorescent protein or GFP. The term "fluorescent protein", as used herein, refers to a protein that has intrinsic fluorescence when excited with electromagnetic radiation at the appropriate wave length. Representative fluorescent proteins can include, but are not limited to, sgGFP, sgBFP, BFP blue-shifted GFP (Y66H), Blue Fluorescent Protein, CFP—Cyan Fluorescent Protein, Cyan GFP, DsRed, monomeric RFP, EBFP, ECFP, EGFP, GFP (S65T), GFP red shifted (rsGFP), GFP wild type, non-UV excitation (wtGFP), GFP wild type, UV excitation (wtGFP), GFPuv, HcRed, rsGFP, Sapphire GFP, sgBFP™, sgBFP™ (super glow BFP), sgGFP™, sgGFP™ (super glow GFP), wt GFP, Yellow GFP and YFP. In a preferred embodiment, the fluorescent protein is GFP.

The term "green fluorescent protein" or "GFP" as used herein refers to a 239 amino acid protein with a molecular weight of 26.9 kDa and which fluoresces bright green when exposed to ultraviolet blue light. Although many other marine organisms have similar green fluorescent proteins, GFP traditionally refers to the protein first isolated from the jellyfish *A. victoria*. GFP from *A. victoria* has a main excitation maximum at a 395 nm wavelength and a minor one at 475 nm. Its emission maximum is at 509 nm. The quantic fluorescence yield of GFP is 0.79. In *A. victoria*, GFP transduces the blue chemiluminescence of aequorin into green fluorescent light by energy transfer.

Alternatively or additionally, the protein of interest may be a protein of therapeutic interest such that the polynucleotide of the invention can be used for expression of said protein in vitro or for the treatment of diseases which require the expression of said protein. Thus, the invention provides polynucleotides comprising one or more polynucleotide of interest that encodes a protein of therapeutic interest including, without limitation, erythropoietin (EPO), leptins, corticotropin-releasing hormone (CRH), growth hormone-releasing hormone (GHRH), gonadotropin-releasing hormone (GnRH), thyrotropin-releasing hormone (TRH), prolactin-releasing hormone (PRH), melatonin-releasing hormone (MRH), prolactin-inhibiting hormone (PIH), somatostatin, adrenocorticotropic hormone (ACTH), somatotropin or growth hormone (GH), luteinizing hormone (LH), follicle-stimulating hormone (FSH), thyrotropin (TSH or thyroid-stimulating hormone), prolactin, oxytocin, antidiuretic hormone (ADH or vasopressin), melatonin, Müllerian inhibiting factor, calcitonin, parathyroid hormone, gastrin, cholecystokinin (CCK), secretin, type I insulin-like growth factor (IGF-I), type II insulin-like growth factor (IGF-II), atrial natriuretic peptide (ANP), human chorionic gonadotropin (hCG), insulin, glucagon, somatostatin, pancreatic polypeptide (PP), leptin, neuropeptide Y, renin, angiotensin I, angiotensin II, factor VIII, factor IX, tissue factor, factor VII, factor X, thrombin, factor V, factor XI, factor XIII, interleukin 1 (IL-1), interleukin 2 (IL-2), tumor necrosis factor-alpha (TNF-α), interleukin 6 (IL-6), Interleukin 8 (IL-8 and chemokins), interleukin 12 (IL-12), interleukin 16 (IL-16), interleukin 15 (IL-15), interleukin 24 (IL-24), interferons-alpha, -beta, -gamma, CD3, ICAM-1, LFA-1, LFA-3, chemokins including RANTES 1α, MIP-1α, MIP-1β, neuronal growth factor (NGF), platelet-derived growth factor (PDGF), transforming growth factor-beta (TGF-beta), bone morphogenic proteins (BMPs), fibroblast growth factors (FGF and KGF), epidermal growth factor (EGF and the like), vascular endothelial growth factor (VEGF), granulocyte colony stimulating factor (G-CSF), glial growth factor, keratinocyte growth factor, endothelial growth factor, alpha-1 antitrypsin, tumor necrosis factor, granulocyte and microphage colony stimulating factor (GM-CSF), cardiotrophin 1 (CT-1), oncostatin M (OSM), amphiregulin (AR), cyclosporine, fibrinogen, lactoferrin, tissue-type plasminogen activator (tPA), chymotrypsin, immunoglobulins, hirudine, dismutase superoxide, imiglucerase, β-glucocerebrosidase, α-L-glycosidase-α, α-L-iduronidase, iduronate-2-sulfatase, galsulfase, human α-galactosidase A, α-1 proteinase inhibitor, lactase, pancreatic enzymes (lipase, amylase, protease), adenosine deaminase, immunoglobulins, albumin, type A and B botulinum toxins, collagenase, human deoxyribonuclease I, hyaluronidase, papain, L-asparaginase, lepirudin, streptokinase, beta cell transformation factor (TGF-β) inhibitor peptides such as those described in WO0331155, WO200519244 and WO0393293, the content of which is incorporated herein by reference, expression cassettes suitable for interference RNA molecule transcription (shRNA, siRNA, miRNA, modified U1 ribonucleoprotein RNA).

In a particular embodiment the polynucleotide of interest is a selection gene, preferably a selection gene that encodes a protein conferring resistance to an antibiotic, more preferable a gene that encodes a protein conferring resistance to neomycin.

In another particular embodiment, the polynucleotide of interest is a polynucleotide encoding a protein of interest, more preferably the green fluorescent protein (GFP).

In one embodiment, the polynucleotide of the invention comprises a first polynucleotide of interest and a second polynucleotide of interest. In this case, the first and second polynucleotide of interest may be operatively linked to the same promoter or each polynucleotide of interest may be operatively linked to separate promoters, which may be identical or different. Any of the promoters mentioned above may be useful for regulating the expression of the first polynucleotide and second polynucleotides of interest.

In a more preferred embodiment, the polynucleotide of the invention comprises a first polynucleotide of interest and a second polynucleotide of interest, wherein the second polynucleotide of interest is operatively linked to the first polynucleotide of interest by a sequence encoding a co-translational self-processing sequence. The term "operatively linked" has been previously defined. The term "co-translational self-processing sequence", as used herein, refers to a polypeptide sequence that directs its own separation from the growing protein during translation. In a particular embodiment, the co-translational self-processing sequence is a "cis-acting hydrolase element" or "chysel element". The term "cis-acting hydrolase element" or "chysel element" refers to a small peptide (usually between 19 and 33 amino acids) that, during its translation, interacts with the exit tunnel of the ribosome to induce the "skipping" of the last peptide bond at the C-terminus of this peptide. Chysel elements are found in some picornavirus, like FMDV, wherein they allow the rapid co-translational self-processing polyproteins. When inserted between two genes, a chysel element induce a "skipping" during its translation after which the ribosome continues to translate the second gene thus producing two discrete proteins. Illustrative non-limitative examples of chysel elements include T2A of Thosea asignavirus, P2A of Porcine teschovirus-1, F2A or E2A of Equine rhinitis A virus). In a particular embodiment, the cis-acting hydrolase element derives from porcine teschovirus. In a more particular embodiment, the sequence encoding a cotranslational self-processing sequence comprises the sequence SEQ ID NO: 11. In an even more particular embodiment, the sequence encoding a cotranslational self-processing sequence consists on the sequence SEQ ID NO: 11.

In a particular embodiment, the polynucleotide of the invention comprises a first polynucleotide of interest, preferably a polynucleotide encoding a protein of interest, more preferably a polynucleotide encoding the GFP, and a second polynucleotide of interest, preferably a selection gene, more preferably a gene encoding a protein conferring resistance to an antibiotic, even more preferably a gene encoding a protein conferring resistance to puromycin, wherein the first and the second polynucleotides of interest are operatively linked by a cotranslational self-processing sequence, preferably a cys-acting hydrolase element derived from porcine teschovirus, more preferably the sequence of SEQ ID NO: 11.

The polynucleotide of the invention can be used to generate a transfer plasmid as a part of a third generation system for generating recombinant lentivirus. Therefore, the polynucleotide of the invention may comprise all the viral processing elements necessary for the production of replication-incompetent lentivirus, as well as elements to improve viral titer and overall vector function.

Thus, in a particular embodiment the polynucleotide of the invention further comprises a primer binding site sequence derived from a lentivirus, wherein said primer binding site sequence is located at a 3' position with respect to the first LTR and at a 5' position with respect to the origin of replication and to the S/MAR, and wherein if the polynucleotide further comprises a polynucleotide sequence selected from a multiple cloning site, a polynucleotide of interest operatively linked to a promoter wherein the promoter is located at a 5' position with respect to the S/MAR and with respect to the origin of replication and at a 3' position with respect to the first LTR and the polynucleotide of interest is located at a 5' position or at a 3' position with respect to the S/MAR and at a 5' position or at a 3' position with respect to the origin of replication and a combination thereof, then the primer binding site is located at a 5' position with respect to said polynucleotide sequence.

The term "primer binding site sequence" or "PBS sequence", as used herein, refers to a polynucleotide sequence which binds the tRNA primer of reverse transcription. In a particular embodiment, the PBS sequence derives from HIV. In a more particular embodiment, the PBS sequence derived from HIV comprises the sequence SEQ ID NO: 12. In an even more particular embodiment, the PBS sequence derived from HIV consists on the sequence SEQ ID NO: 12.

In a particular embodiment, the polynucleotide of the invention further comprises a packaging signal sequence derived from a lentivirus located between the first and the second LTR. The term "packaging signal sequence", as used herein, refers to a polynucleotide sequence that allows the encapsidation of the viral RNA into virions. In a particular embodiment, the packaging signal sequence is the ψ sequence derived from HIV. In a more particular embodiment, the packaging signal sequence derived from HIV comprises the sequence SEQ ID NO: 13. In an even more particular embodiment, the packaging signal sequence derived from HIV consists on the sequence SEQ ID NO: 13. In a preferred embodiment, the packaging signal sequence is located in the vicinity of the first LTR. In another preferred embodiment, the packaging signal sequence is located in the vicinity of the second LTR.

In a particular embodiment, the polynucleotide of the invention further comprises a Rev response element (RRE) derived from a lentivirus located between the first and the second LTR. The term "rev response element" or "RRE", as used herein, refers to a polynucleotide sequence that enhances the transport of unspliced viral RNA out of the nucleus increasing viral titers. In a particular embodiment, the RRE derives from HIV. In a more particular embodiment, the RRE from HIV comprises the sequence SEQ ID NO: 14. In an even more particular embodiment, the RRE from HIV consists on the sequence SEQ ID NO: 14. In a particular embodiment, the RRE is located between a splice donor site and a splice acceptor site. The term "splice donor site" or "SD", as used herein, refers to refers to a sequence or domain of a nucleic acid present at the 5' end of an intron that marks the start of the intron and its boundary with the preceding coding sequence or exon. The term "splice acceptor site" or "SA", as used herein, refers to a sequence or domain of a nucleic acid present at the 3' end of an intron that marks the start of the intron and its boundary with the following coding sequence (exon). In a particular embodiment de SD is the 5' splice site of the gag gene in the HIV-1 genome. In a particular embodiment, the AD is the 3' splice site of the pol gene in the HIV-1 genome. For a detailed description of HIV-1 genome SD and AD see, for example, Kammler et al., Retrovirology 2006, 3:89.

In a particular embodiment, the polynucleotide of the invention further comprises a central polypurine tract (cPPT) derived from a lentivirus, wherein said central polypurine tract is located at a 3' position with respect to the first LTR and at a 5' position with respect to the origin of replication and to the S/MAR, and wherein if the polynucleotide further comprises a polynucleotide sequence selected from a multiple cloning site,
a polynucleotide of interest operatively linked to a promoter wherein the promoter is located at a 5' position with respect to the S/MAR and with respect to the origin of replication and at a 3' position with respect to the first LTR and
the polynucleotide of interest is located at a 5' position or at a 3' position with respect to the S/MAR and at a 5' position or at a 3' position with respect to the origin of replication and
a combination thereof, then the central polypurine tract is located at a 5' position with respect to said polynucleotide sequence. The term "central polypurine tract" or "cPPT", as used herein, refers to a polynucleotide sequence that, during cell infection creates a central DNA flap that increases nuclear import of the viral genome, resulting in a more efficient transduction. In a particular embodiment, the cPPT derives from HIV. In a more particular embodiment, the cPPT from HIV comprises the sequence of SE ID NO: 15. In an even more particular embodiment, the cPPT from HIV comprises the sequence of SEQ ID NO: 15.

In a particular embodiment, the polynucleotide of the invention comprises PBS sequence, a packaging signal sequence, a RRE and a cPPT, preferably the PBS sequence of SEQ ID NO: 12, the packaging signal sequence of SEQ ID NO: 13, the RRE of SEQ ID NO: 14 and the cPPT of SEQ ID NO: 15.

The polynucleotide of the invention can also comprise the elements necessary for its propagation in prokaryotes. Thus, in a particular embodiment, the polynucleotide of the invention further comprises a prokaryotic origin of replication and a selection marker. The term "prokaryotic origin of replication", as used herein, refers to a particular sequence at which the replication is initiated in prokaryotes. Illustrative non limitative examples of origins of replication in prokaryotes are the pUC origin derived from pBR322 in *E. coli*; pSC101 derived from *Salmonella* and 15A origin derived from p15A. The term "prokaryote" as used herein, comprises the domains Bacteria and Archaea. In a particular embodiment, the prokaryotic origin of replication is the origin of the pUC vector. In a more particular embodiment, the prokaryotic origin comprises the sequence of SEQ ID NO: 16. In an even more particular embodiment, the prokaryotic origin consists on the sequence of SEQ ID NO: 16. The term "selection marker" has been described in detail above and is equally applicable. In a particular embodiment, the selection marker is a gene that encodes a protein conferring resistance to an antibiotic. In a more particular embodiment, the selection marker that encodes a protein conferring resistance to an antibiotic is a gene encoding a protein that confers resistance to ampicillin.

Vector of the Invention

In another aspect, the invention relates to a vector, hereinafter vector of the invention, comprising the polynucleotide of the invention. The term "vector", as used herein, refers to a construct capable of delivering, and optionally expressing, one or more polynucleotides of interest into a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vector can be a cloning vector or an expression vector. The term "cloning vector", as used herein, refers to a vector suitable for propagation and to obtain the adequate polynucleotides or gene constructs or expression vectors in different heterologous organisms suitable for the purification of the vector. The term "expression vector", as used herein, refers to a vector suitable for expression of a polynucleotide in a target cell. The expression vector of the invention is a lentiviral vector. The term "lentiviral vector", as used herein, refers to a nucleic acid sequence comprising the necessary sequences so that after transcribing and translating said sequences in a cell with expression of the lentiviral genes gag, pol, rev and a gene encoding an envelope viral protein, a viral particle with capacity for infecting a new cell is generated.

The vectors of the invention can be obtained by means of techniques widely known in the art. See Brown T, "Gene Cloning" (Chapman & Hall, London, G B, 1995); Watson R, et al., "Recombinant DNA", 2nd Ed. (Scientific American Books, New York, N.Y., US, 1992); Alberts B, et al., "Molecular Biology of the Cell" (Garland Publishing Inc., New York, N.Y., US, 2008); Innis M, et al., Eds., "PCR Protocols. A Guide to Methods and Applications" (Academic Press Inc., San Diego, Calif., US, 1990); Erlich H, Ed., "PCR Technology. Principles and Applications for DNA Amplification" (Stockton Press, New York, N.Y., US, 1989); Sambrook J, et al., "Molecular Cloning. A Laboratory Manual" (Cold Spring Harbor Laboratory Press, Cold Spring Harbor, N.Y., US, 1989); Bishop T, et al., "Nucleic Acid and Protein Sequence. A Practical Approach" (IRL Press, Oxford, G B, 1987); Reznikoff W, Ed., "Maximizing Gene Expression" (Butterworths Publishers, Stoneham, Mass., US, 1987); Davis L, et al., "Basic Methods in Molecular Biology" (Elsevier Science Publishing Co., New York, N.Y., US, 1986), Schleef M, Ed., "Plasmid for Therapy and Vaccination" (Wiley-VCH Verlag GmbH, Weinheim, D E, 2001).

Cell of the Invention

The polynucleotide of the invention and the expression vector comprising said polynucleotide can be used to transform, transfect or infect cells which can be transformed, transfected or infected by said polynucleotide or vector. Therefore, in another aspect, the invention relates to a cell, hereinafter cell of the invention, comprising a polynucleotide of the invention or a vector comprising the nucleotide of the invention.

The cell of the invention can be obtained introducing in a cell the polynucleotide of the invention or the vector of the invention by techniques well known by the skilled person such as infection, transduction, transfection, electroporation and transformation using the polynucleotide of the invention isolated, incorporated into artificial liposomes or forming part of the vector of the invention.

The cell of the invention can be either a prokaryotic or a eukaryotic cell. The terms "prokaryotic" and "eukaryotic" have been previously defined. In a particular embodiment, the cell of the invention is a eukaryotic cell. In a more particular embodiment, the eukaryotic cell is a packaging cell, i.e. a cell that allows for production of recombinant viral vectors by transfection with the polynucleotide of the invention or with the lentiviral vector of the invention. In a particular embodiment, the packaging cell is the human embryonic kidney cell line 293 (HEK293). In a more particular embodiment, the packaging cell is the human embryonic kidney cell line 293 that comprises the SV40 large T-antigen (HEK293T).

Recombinant Lentivirus of the Invention and In Vitro Method for Generating the Same The polynucleotide of the invention, or the vector comprising said polynucleotide, can be used to generate a recombinant lentivirus by transfection of said polynucleotide, or the vector comprising said polynucleotide, in a cell that expresses the product of the lentiviral genes gag, pol, rev and an envelope viral protein.

Thus, in another aspect, the invention relates to a recombinant lentivirus, hereinafter recombinant lentivirus of the invention, comprising a polynucleotide of the invention and a lentiviral integrase comprising a mutation that causes said integrase to be unable to catalyze the integration of the viral genome into a cell genome.

The term "recombinant lentivirus", as used herein, refers to a lentivirus comprising at least one heterologous polynucleotide. The term "lentivirus" has been previously defined.

The term "lentiviral integrase", as used herein, refers to the gene product of the int region of a lentivirus, particularly of the HIV-1 virus, characterized by having three clearly identifiable domains: the central catalytic core domain flanked by the N-terminal and C-terminal domains, the latter involved in DNA binding. A single polypeptide chain of most retroviral integrase comprises approximately 290 residues. Some important variations are, however, present. For example, PFV integrase is significantly longer, comprising 392 residues, and ASV integrase is encoded as a 323-amino acid long protein that is post-translationally processed to the final polypeptide consisting of 286 residues, which is fully enzymatically active. Particularly, the integrase of HIV-1 virus is the gene product of the int region of the virus, having 288 amino acids and designated as IN. In a particular embodiment, the lentiviral integrase is the HIV-1 integrase comprising a mutation that causes said integrase to be unable to catalyze the integration of the viral genome into a cell genome. The term "HIV-1integrase", as used herein, refers to the mature processed form of the HIV-1 integrase polypeptide defined under accession number C7B8I1 in the Uniprot database (release Oct. 16, 2013, Version 27). The term HIV-1 integrase is also used to refer to HIV-1 integrase from other strains or isolates of the virus. The nucleic acid and amino acid sequence of a large number of HIV-1 integrases are readily available to the public. See HIV Sequence Database, http://www.hiv.lanl.gov/content/sequence/HIV/mainpage.html; Los Alamos HIV Databases and Compendia, http://www.hiv.lanl.gov/.

The lentiviral integrase of the recombinant lentivirus of the invention comprises a mutation that causes said integrase to be unable to catalyze the integration of the viral genome into a cell genome. In a preferred embodiment, said mutations are type I mutations, i.e., mutations affecting directly the integration as opposed to type II mutations which trigger pleiotropic defects affecting virion morphogenesis and/or reverse transcription. Illustrative non-limitative examples of type I mutations are those mutations affecting any of the three residues that participate in the catalytic core domain of the integrase: $DX_{39-58}DX_{35}E$ (D64, D116 and E152 residues of the integrase of the HIV-1). In a particular embodiment, the mutation that causes said integrase to be unable to catalyze the integration of the viral genome into a cell genome is the substitution of one or more amino acid residues of the DDE motif of the catalytic core domain of the integrase, preferably the substitution of the first aspartic residue of said DEE motif by an asparagine residue. In a particular embodiment, the integrase comprises the sequence of SEQ ID NO: 17. In a more particular embodiment, the integrase consists on the sequence of SEQ ID NO: 17.

In a particular embodiment, the recombinant lentivirus of the invention comprises an envelope glycoprotein G from a vesicular stomatitis virus (VSV). The term "glycoprotein G", as used herein, refers to a protein from the envelope of the VSV that enables viral entry, since mediates viral attachment to the host cell, where the virus is endocytosed, and then mediates fusion of the viral envelope with the endosomal membrane (e.g. Uniprot KB database accession no. Q6EH37). The term glycoprotein G is also used to refer to VSV glycoprotein G from other strains or isolates of the virus and also to functionally equivalent variants thereof. As it is used herein, "functionally equivalent variant of VSV glycoprotein G" is understood as a polypeptide capable of complementing the temperature-sensitive G mutant of VSV tsO45 at a nonpermissive temperature and having a minimal identity in the amino acid sequence with the sequence of the VSV glycoprotein G. See Lefkowitz E, et al., Virology 1990; 178(2):373-383. The functionally equivalent variants of VSV glycoprotein G include polypeptides showing at least 60%, 65%, 70%, 72%, 74%, 76%, 78%, 80%, 90%, 95%, 97%, 99% similarity or identity with the different natural variants of glycoprotein G mentioned above. The variants of VSV glycoprotein G can be both natural and artificial. The expression "natural variant" refers to all those variants of VSV glycoprotein G defined above which occur naturally in other strains. The expression "artificial variant" refers to a recombinant or synthetic polypeptide. The terms "VSV" or "vesicular stomatitis virus", as used herein, refer to negative-stranded RNA virus of approximately 11 kb in size of the rhabdoviridae family. VSV is also known as "vesicular stomatitis indiana virus" or "VSIV". At present, eight VSV subtypes have been described in the art. See http://viralzone.expasy.org/complete_by_species/21.html#tab6, October 2013.

In another aspect, the invention relates to an in vitro method for generating the recombinant lentivirus of the invention comprising
  (i) contacting an eukaryotic cell with the polynucleotide of the invention or with the vector of the invention, wherein the cell expresses the products of the lentiviral genes gag, pol, rev and a viral envelope protein under conditions adequate for entry of the polynucleotide or vector in said cell and
  (ii) maintaining the cell under conditions adequate for assembly of the lentivirus.

The term "in vitro method" implies that said method is not carried out on the body of a subject, human or animal, but on cells isolated from said subject.

The terms "recombinant lentivirus" and "eukaryotic cell". In a particular embodiment, the eukaryotic cell is a packaging cell, i.e. a cell that allows for production of recombinant viral vectors by transfection with the polynucleotide of the invention or with the lentiviral vector of the invention. In a particular embodiment, the packaging cell is the human embryonic kidney cell line 293 (HEK293). In a more particular embodiment, the packaging cell is the human embryonic kidney cell line 293 that comprises the SV40 large T-antigen (HEK293T) that allows for episomal replication of transfected plasmids containing the SV40 origin of replication.

The term "gag", as used herein, refers to the gene encoding the p55 protein of the capsid formed by 3 protein subunits (MA, CA, and NC). In particular embodiment, the gag gene derives from HIV-1.

The term "pol", as used herein, refers to the gene encoding the viral enzymes necessary for the viral replication process: protease (PRO), reverse transcriptase (RT), and integrase (INT). In particular embodiment, the pol gene derives from HIV-1.

The term "rev", as used herein, refers to the gene encoding the Rev protein responsible for processing messenger RNA and transporting it to the cytoplasm. In particular embodiment, the rev gene derives from HIV-1.

The term "envelope" or "viral envelope", as used herein, relates to the viral structure covering the viral capsid that typically is derived from portions of the host cell membranes. The viral envelope comprises phospholipids and proteins from the membrane of the host cell, and may include as well viral glycoproteins. The term "viral envelope protein", as used herein, relates to a protein constituent of the viral envelope. In a preferred embodiment, the envelope viral protein is the glycoprotein G from vesicular stomatitis virus (VSV). The terms "glycoprotein G" and "vesicular stomatitis virus" have been previously defined.

The term "conditions adequate for entry", as used herein, means those conditions known by the skilled person by which a polynucleotide or vector can entry a eukaryotic cell. Illustrative non-limitative examples of techniques that can be used for introducing polynucleotides or vectors into a eukaryotic cell include infection, transduction, transfection, electroporation and transformation using polynucleotide of the invention, either isolated or incorporated into artificial liposomes or as a part of the aforementioned vector.

According to the first step of the method for generating the recombinant lentivirus of the invention, the polynucleotide or vector of the invention is contacted with a eukaryotic cell that expresses the products of the lentiviral genes gag, pol, rev and the product of the gene encoding the envelope glycoprotein G from vesicular stomatitis virus. Said cell can be obtained by contacting a eukaryotic cell with one or more polynucleotides comprising the lentiviral genes gag, pol and rev and the gene encoding the envelope glycoprotein G from VSV. Any of the above mentioned techniques for introducing a polynucleotide into a eukaryotic cell can be used to obtain the eukaryotic cell comprising the product of the lentiviral genes gag, pol and rev and the product of the gene encoding the envelope glycoprotein G from VSV. In a particular embodiment, said cell is obtained by transfection with one or more polynucleotides, preferably one or more vectors, comprising the lentiviral genes gag, pol and rev and the gene encoding the envelope glycoprotein G from VSV. In a particular embodiment, the cell is obtained by transfection with the following polynucleotides:
  a polynucleotide or vector comprising the rev gene
  a polynucleotide or vector comprising the gene encoding the envelope glycoprotein G from VSV and
  a polynucleotide or vector comprising gag and pol genes.

In a particular embodiment, the polynucleotide or vector comprising the gag and pol genes further comprises a rev response element (RRE). The term "rev response element" has been previously defined.

In a particular embodiment, the eukaryotic cell comprising the product of the lentiviral genes gag, pol and rev and the viral envelope protein is obtained by co-transfection with the above mentioned polynucleotides or vectors. Said cell can be used for carrying out the in vitro method for generating the recombinant lentivirus of the invention. Thus in a particular embodiment, the cell that expresses the products of the lentiviral genes gag, pol, rev and the viral envelope protein has been transfected with one or more polynucleotides encoding the gag gene, the pol gene, the rev gene and with a polynucleotide encoding the viral envelope protein prior to the contacting with the polynucleotide or with the vector of the invention.

In another particular embodiment, the cell is simultaneously contacted with the polynucleotide or vector of the invention and with one or more polynucleotides, preferably one or more vectors, comprising the lentiviral genes gag, pol and rev and the gene encoding the viral envelope protein. In a more particular embodiment, the cell is co-transfected with the polynucleotide or vector of the invention and with one or more polynucleotides, preferably one or more vectors, comprising the lentiviral genes gag, pol and rev and the gene encoding the viral envelope protein. In an even more particular embodiment, the cell is co-transfected with the following polynucleotides:
  the polynucleotide or vector of the invention,
  a polynucleotide or vector comprising the rev gene,
  a polynucleotide or vector comprising the gene encoding the viral envelope protein and
  a polynucleotide or vector comprising gag and pol genes.

The step (ii) of the in vitro method for generating the recombinant lentivirus of the invention comprises maintaining the cell obtained by step (i) under conditions adequate for assembly of the lentivirus. The term "conditions adequate for assembly of the lentivirus" means those conditions known by the skilled person that allow the expression of the viral proteins and the assembly of new viral particles that are released into the culture medium of the cells. These conditions will vary depending on the type of cell. Exemplary conditions which promote the release of the recombinant lentivirus into culture medium may be carried out as described in examples herein. Producer cells are grown for a suitable period of time in order to promote release of viral vectors into the media. Generally, cells may be grown for about 12 hours, about 24 hours, about 36 hours, about 48 hours, about 72 hours. When the cell is HEK293T, the conditions adequate for assembly of the lentivirus comprise incubating the cells in fresh culture medium under standard culture conditions for several hours post-transfection, preferably between about 24 and about 48 hours post-transfection, more preferably for about 48 hours post-transfection.

In a particular embodiment, the in vitro method for generating the recombinant lentivirus of the invention further comprises purifying the recombinant lentivirus produced by the cell. Said purification can be carried out by any suitable method known by the skilled person. Illustratively, the purification of the recombinant lentivirus can be performed by collection of the culture medium of the cells obtained after step (ii) of the in vitro method and low-speed centrifugation and filtration of said medium. Optionally, viral stocks can be concentrated by ultracentrifugation.

Stable Cells and Cell Populations of the Invention, In Vitro Method for Generating the Same and Use of the Same for the In Vitro Production of a Product of Interest When the recombinant lentivirus of the invention comprises the polynucleotide of the invention comprising a polynucleotide of interest, said recombinant lentivirus can be used for obtaining a cell line that stably expresses said polynucleotide of interest. Thus, in another aspect the invention relates to a stable cell, hereinafter stable cell of the invention, which can express a polynucleotide of interest comprising the polynucleotide of the invention wherein said polynucleotide comprises the sequence of a polynucleotide of interest operatively linked to a promoter wherein
    the promoter is located at a 5' position with respect to the S/MAR and with respect to the origin of replication and at a 3' position with respect to the first LTR and
    the polynucleotide of interest is located at a 5' position or at a 3' position with respect to the S/MAR and at a 5' position or at a 3' position with respect to the origin of replication.

The term "stable cell", as used herein, relates to a cell that exhibits expression of a polynucleotide of interest along successive passages. In preferred embodiments, the cells show expression of the polynucleotide of interest at least 50 days, at least 60 days, at least 70 days, at least 80 days, at least 90 days post-transduction of the cell with the recombinant lentivirus of the invention. In preferred embodiments, the cells show expression of the polynucleotide of interest at least after 2, 4, 6, 8, 10, 20, 30, 40, 50, 60, 70, 80, 90, 100, 1000, 5000, 10000 or more passages post-transduction of the cell with the recombinant lentivirus of the invention.

In another aspect the invention relates to a stable cell population which comprises a plurality of the cells of the invention. In a particular embodiment, the stable cell population of the invention contains at least a 30%, at least a 40%, at least a 50%, at least a 60%, at least a 70%, at least a 80%, at least a 90%, at least a 95%, up to 100% of the cells stably express the polynucleotide of interest.

In a particular embodiment, the stable cell is a eukaryotic cell, preferably a mammalian cell. In a more particular embodiment, the mammalian cell is the human embryonic kidney cell line 293 that comprises the SV40 large T-antigen (HEK293T) that allows for episomal replication of transfected plasmids containing the SV40 origin of replication.

The terms "promoter", "operatively linked", "S/MAR", "origin of replication" and "first LTR" have been previously defined.

In another aspect, the invention relates to an in vitro method for generating the stable cell population of the invention comprising the steps of
    (i) contacting cells with the recombinant lentivirus of the invention, wherein the recombinant lentivirus comprises the sequence of a polynucleotide of interest operatively linked to a promoter wherein
        the promoter is located at a 5' position with respect to the S/MAR and with respect to the origin of replication and at a 3' position with respect to the first LTR and
        the polynucleotide of interest is located at a 5' position or at a 3' position with respect to the S/MAR and at a 5' position or at a 3' position with respect to the origin of replication, and
    (ii) growing and maintaining the cells.

The terms "in vitro method", "stable cell population", "recombinant lentivirus", "polynucleotide of interest", "promoter", "operatively linked", "S/MAR", "origin of replication" and "first LTR" have been previously defined.

The step (i) of the in vitro method for generating the stable cell population of the invention comprises contacting cells with the recombinant lentivirus of the invention comprising a polynucleotide of interest operatively linked to a promoter, so that the cell is transduced. The term "transduction", as used herein, refers to the process whereby a foreign polynucleotide sequence is introduced into a cell via a viral vector. Suitable conditions for transducing a cell with a recombinant lentivirus are known by the skilled person. By way of illustration, it can be carried out, for example, by incubating cells with lentiviral supernatant for 4-6 hours at 37° C. in a cell culture incubator in the presence of 8 µg/mL Polybrene™, as explained in the examples of the present application.

The step (ii) of the in vitro method for generating the stable cell population of the invention comprises growing and maintaining the cells. The conditions for the growing and maintenance of the cells vary depending on the cell type and are known by the skilled person.

Although not strictly necessary for the generation of a stable cell population, it is possible to select those cells that have been transduced with the recombinant lentivirus of the invention. Thus, in a particular embodiment the method for generating the stable cell population of the invention further comprises selecting the cells generated in step (i). The selection can be done by any technique known in the art adequate for the selection of cells expressing a particular polynucleotide. For example, clones may be obtained from the cells resulting from step (i) of the method for the generation of a stable cell population by, for example, limiting dilution of the cells. Such clones may be analyzed to detect the incorporation of the polynucleotide of the invention by any technique known to those skilled in the art suitable for the detection of specific sequences of polynucleotides, for example by polymerase chain reaction (PCR), or may be analyzed for the presence a protein encoded by the polynucleotide of the invention by any technique known to those skilled in the art suitable for detection of proteins, for example, immunofluorescence, flow cytometry, immunoblotting, etc.

When the polynucleotide of the invention comprises a selection gene, the selection can be carried out by putting the cells under restrictive conditions according to the type of the selection gene, i.e., conditions in which gene expression suppose a selection advantage to cells. For example, if the polynucleotide of the invention comprises a selection gene that allows synthesizing a nutrient, the selection would comprise putting the cells in a medium lacking said nutrient. When the polynucleotide of the invention comprises a selection gene whose expression confers resistance to an antibiotic, the selection would comprise putting the cells in a culture medium comprising said antibiotic.

In a particular embodiment, the polynucleotide of the invention comprises a selection gene conferring resistance to an antibiotic, preferably neomycin, so that the selection would comprise placing the cells in a culture medium containing neomycin. When the polynucleotide of the invention comprises a gene encoding a fluorescent protein, the selection can be done by fluorescence-activating cell sorting (FACS).

In another aspect, the invention relates to the use of the stable cell population of the invention for the in vitro production of a product of interest or to an in vitro method for the production of a product of interest comprising culturing a stable cell population of the invention under conditions allowing the expression of the polynucleotide of interest.

The terms "stable cell population" and "in vitro method" have been previously defined. The term "product of interest", as used herein, refers to product of any polynucleotide whose expression in a cell is desirable. The product of interest can be a polypeptide or protein of interest or a polynucleotide that, once transcribed, generates a RNA which is able to hybridize with a mRNA inhibiting its expression like, for example, a microRNA, a siRNA or a shRNA. In a particular embodiment, the product of interest is a protein of interest. In a more particular embodiment, the protein of interest is a fluorescent protein. In an even more particular embodiment, the product of interest is the green fluorescent protein (GFP). The terms "protein of interest", "fluorescent protein" and "GFP" have been previously defined.

The invention is described by way of the following examples, which are merely illustrative and no limitative of the scope of the invention.

EXAMPLES

Materials and Methods
Mammalian Cell Culture and Transfection

The human embryonic kidney cell line HEK293A (CRL-1573, ATCC) was cultured under standard conditions in DMEM (Lonza, Lonza Ibérica S A, Barcelona, Spain) supplemented with 1% Glutamax (Invitrogen, Prat del Llobregat, Barcelona, Spain), 10 mg/ml antibiotics (penicillin and streptomycin) and 10% fetal bovine serum (Gibco, Invitrogen). When cells were cultured under selective conditions medium was replaced by DMEM with G418 (Geneticin, Invitrogen, LifeTechnologies) at a 450 µg/ml.

Lentivirus Generation by Transfection

Viruses were produced by four-plasmid transient transfection into HEK293T cells by the calcium phosphate method. Cells were seeded at $1.1 \times 10^7$ cells/dish in 15-cm dishes the day before transfection. Cells were transfected with endotoxin-free DNA (Qiagen, Las Matas, Madrid, Spain). Transfection cocktail was 1×HBS, 0.125 $CaCl_2$ containing 3 µg pRSV-Rev, 3.75 µg pMD.2G (VSV-G), 13 µg pMDLg/pRRE or 13 µg pMDLg/pD64VRRE for production of non-integrative lentiviral vectors, and 35 µg of transfer plasmid (pLS series). The cocktail was prepared with 82 µL plasmid DNA, 476 µL of $CaCl_2$ 2.5M and 3343 µL milliQ water and mixed by drop with 3900 µL of 2×HBS pH 7.02. The transfection mix was added drop wise to the cells. Cells were incubated with the transfection mix for 4-6 h in the incubator and then washed and the medium changed. The medium was collected after 48 h, cleared by low-speed centrifugation, and filtered through 0.45-mm-pore-size PVDF filters. Viral stocks were concentrated by ultracentrifugation in SW28 Beckman rotor at 90.000 g (26.000 rpm) for 2 h at 4° C. Pellets containing lentiviruses were air dried and resuspended overnight at 4° C. in 400-600 µl of media.

Lentiviral Titration and Transduction

Biological viral titers were calculated by transduction at several dilutions on reference HEK293T cells and analysis by FACS (transduction units/ml, T.U./mL) as follows. One day before the transduction $2 \times 10^5$ reference cells were seed on 6-well multi-well plates and inoculate by replacing media with 1 mL of lentiviral supernatant diluted regularly at ⅒, ¹⁄₁₀₀ and ¹⁄₁₀₀₀ in medium with 8 µg/mL Polybrene™ for 4-6 h at 37° C. in the incubator. Inoculum was replaced with normal medium and cells were cultivated for 48 h before FACS.

Total genome-containing particles were quantitated by qPCR on supernatants (particles/mL). Denatured particles at dilutions ranging ⅒ to ¹⁄₁₀₀₀ were used as template in a qPCR reaction (see below for primers and specific conditions used). Standard curves were obtained running plasmid template at 1 ng to 1 pg range of dilutions and reference values plotted. Test raw data was interpolate in the curve and transformed into copies/cell.

Regular values were around 107-108 T.U./ml in a 1:100 particles to T.U. ratio.

Genomic DNA Extraction

Cells ($5\text{-}10 \times 10^6$) were either trypsinized or scraped and transferred to a 13 mL-PE conical tube conical tube washed in PBS and pelleted in a top bench centrifuge at low speed (1,500 rpm). Pellet was resuspended in lysis buffer (100 mM NaCl, Tris pH8.0 50 mM, EDTA 100 mM and 1% SDS), transferred to a microtube and digested with proteinase K (0.5 µg/mL) overnight at 56° C. with low agitation. Afterward 250 µL of saturated NaCl was added, mixed and let 5 min at room temperature before centrifuge at 13,000 rpm in minifuge. 750 µL of the supernatant was extracted without disturbing the pellet and precipitated with 500 µL of iso-propanol, mixed and spun down at 13,000 rpm at RT, washed with 70% ethanol, air dried and resuspended overnight at RT in 1×TE. Serial dilutions of the resuspended DNA were quantitated using NanoDrop ND 1000 Spectrophotometer (NanoDrop Technologies, Bonsai Technologies Group SL, Alcobendas, Madrid, Spain).

Hirt's Extraction

Trypsinized cells (typically $5\text{-}10 \times 106$ cells) were transferred to a 13 mL-PE conical tube and pelleted for 3-5 min in top-bench centrifuge at low speed (1000-1500 rpm) at RT. The pellet was washed with cold PBS and centrifuged as before. Resuspended pellet was transferred to a microcentrifuge tube and centrifuged at 13.000 rpm for 5 min at 4° C. The pellet was resuspended in Hirt's lysis buffer (0.6% SDS and 10 mM EDTA) without pipetting or vortexing and incubated 15 min at RT. Genomic DNA was precipitated by adding 5M of NaCl to a final concentration of 1.4 M, mixed gently by inversion and stored overnight at 4° C. Proteins and genomic DNA was centrifuged at 13.000 rpm in a microcentrifuge for 30-60 min at 4° C. The supernatant containing low molecular DNA was phenol extracted, ethanol precipitated and resuspended in 100-200 µL of water.

Southern Blot

Digested samples were loaded on a 0.8% agarose gel in 1×TAE and separated by running at 70-100 V constant voltage until the dye front is 1-3 cm from the end of the gel.

Control, quantitated plasmids containing the sequences to be detected was loaded to provide a reference for size and quantity (20 pg, 200 pg and 2 ng). The gel was photographed under 300 nm ultraviolet light. The gel was washed in distilled water and then equilibrated in 2×SSC for 15 min at RT. The gel was blotted by capillarity on nylon membranes Hybond-N plus (GE Healthcare) with NaOH 0.5N overnight at RT. The membrane was fixed by irradiation a in a Stratalinker (Stratagene) and used for further hybridization.

The probes used were the purified products of restriction endonuclease digestion of the plasmids pcDNA3.1 (Xmai-BstBI, 0.8 Kpb) (Invitrogen) for neo and pZDonor AAVS1 (KpnI-XmaI, 0.7 Kpb) (Sigma Aldrich) for AAVS1 detection. Labelling was performed using 100 µCi/reaction of 32P-alphaCTP using the commercial kit RediPrime II (GE Healthcare) following the manufacturer instructions. Non-incorporated nucleotides were removed using a Micro Bio-Spin P-30 (BioRad) column according to manufacturer's instructions and quantitated by scintillation counting. Filters were wetted in 2×SSC and prehybridized and hybridized in 25 cm tubes with 10-20 mL of PerfectHyb™ Plus (Sigma Aldrich). Hybridization solution contained $1\text{-}2\times10^7$ cpm/mL and was left to proceed overnight at 66° C. Filters were then washed with successive 20 minute-washes at 65° C. in 0.1×SSC 0.5% SDS. Wet membranes were exposed to PhosphorImager screen and developed using STORM scanner.

Real-Time PCR

The quantitative PCR to determine the non-integrated 2-LTR episomal forms derived from transduced cultures with LentiSome was performed using the SYBR Green methodology described in Butler, S L et al., J. Virol. 2002, 76(8): 3739. DOI: 10.1128/JVI.76.8.3739-3747.2002. The number of copies of albumin in the HEK293A cells was measured as previously described with some modifications. In all assays PCR efficiency was determined with serial dilutions of standardized DNAs and the specificity of individual gene primers was validated by the melting curve at the end of each qPCR assay. Standard curves were obtained with diluted amounts of the pRR1.sin18.CMV.eGFP.Wpre plasmid (Addgene) that range from 0.01 pg to 100 ng, which correspond to $10^2\text{-}10^9$ copies. Ct values obtained upon amplification of using the specific primers listed below were interpolated and the absolute number of copies in experimental samples calculated. Cell equivalents were calculated using Ct values similarly with the albumin single copy gene on diluted test samples of the genomic DNA and standardized genomic DNA. Positive control to 2-LTR qPCR was a fragment containing the LTR-LTR element synthesised and cloned in a regular plasmid.

The primers used were:

```
                                        (SEQ ID NO: 18)
    qLTR Fw: TGTGTGCCCGTCTGTTGTGT (SEQ ID NO: 19)
    qLTR Rv: GAGTCCTGCGTCGAGAGAGC
```

Amplicon size: 95 bp

```
                                        (SEQ ID NO: 20)
    qhAlb Fw: GCTGTCATCTCTTGTGGGCTGT (SEQ ID NO: 21)
    qhAlb Rv: ACTCATGGGAGCTGCTGGTTC
```

Amplicon size: 124 bp

```
                                        (SEQ ID NO: 22)
    q2LTR R Rv2: TGAAGCACTCAAGGCAAGCTTTATT (SEQ ID NO: 23)
    q2LTR U5 Fw2: GTGTGTGCCCGTCTGTTGTGTGACT
```

Amplicon size: 231 bp

Cytometer Analysis

Flow cytometry analysis was performed after 72 hours post-transduction. Cells were trypsinized and collected, washed twice in culture-grade 1×PBS and analyzed in a FACS DIVA (Becton Dickinson, San Agustín de Guadalix, Madrid, Spain) sorter with an appropriate laser for CherryFP excitation. In every case, 10,000 events were counted in triplicate.

Karyotyping

The cell line was incubated at 37° C. in culture flasks in an atmosphere of 5% $CO_2$ in air. Metaphase cells were prepared by standard cytogenetic methods. Mitotic arrest with colcemid (0.1 µg/mL, 1.5 hours, 37° C.; GIBCO, Strachclyde, UK) was followed by hypotonic treatment (75 mm KCl, 15 minutes, 37° C.) and fixation with methanol/acetic acid (3:1) before spreading onto slides.

Fluorescence In Situ Hybridization Analysis (FISH)

For FISH analysis, cells were first treated with colcemid (Invitrogen), and then harvested after a treatment with a hypotonic salt solution.

A set of probes was used to localize virus integration sites. LentiSome integration site was detected using the DNA from the vector plasmid. A bacterial artificial chromosome (BAC), RP11-49L9, that maps at 4q13.3 cytoband was used as control. The BAC was obtained from the Human BAC Clone Library RPCI-11 (Children's Hospital Oakland Research Institute, Oakland, Calif.). 1 g of plasmid or BAC DNA was directly labeled using Nick Translation Kit (Cat #: 07J00-001, Vysis). This kit is designed for fluorescence labeling of DNA using fluorophore-labeled dUTPs (SpectrumGreen- or Spectrum Orange). The labeled DNAs were co-precipitated with Cot-1DNA and DNA sheared salmon sperm (Vysis, Dowers Grove, Ill., USA) to prevent the unspecific hybridization in genomic repetitive DNA sequences. The precipitated DNA mixture was resuspended in hybridization mix.

To perform the FISH reaction, the probe and metaphase spreads were heated, co-denatured and hybridized overnight at 37° C. After two post-hybridization washes with 0.4× SSC/0.3% NP40 and 2×SSC/0.1% NP40, the chromosomes were counterstained with DAPI in anti-fade solution (Abbott Molecular).

Cell images were captured using a cooled charge-coupled device (CCD) camera (Photometrics SenSys camera) connected to a computer running the Chromofluor image analysis system (Cytovision, Applied Imaging Ltd, Newcastle, UK).

Results

Example 1: Lentiviral-Episomal (LentiSome) Maintenance in Highly Cycling Cells

Description of the Approach

We have systematically analyzed the effect of a series of combinations of mammalian ori and S/MAR sequences on the maintenance and segregation of the episomal 1-, 2-LTRs in exponentially growing cells along dozens of population doublings spanning two months in culture.

From a short but well characterized collection of sequences proved as either ori or S/MAR, we have selected a few sharing two major features. First, the length of both sequences must be limited to a size capable to be accommodated in a lentiviral vector as other sequences of interest will be further cloned in the lentiviral vector and second, the eukaryotic non viral-derived nature of the ori/SMAR elements. Tough the best-characterized ori sequences are derived from DNA viruses; the major drawback to be used in the clinic is their strict requirements of viral proteins to be functional activated as SV40 large T antigen, papillomavirus E1/E2 proteins or herpesvirus EBNA. However, all of them promote inevitably cell transformation of cells expressing such genes. The eukaryotic nature implies that they have been proved functional in mammalian cells and responders to cellular signals triggered to replicate in a rate of one-per-cell-cycle.

The three ori sequences we have selected matching such features map at the human beta-globin locus (Kitsberg D et al., Nature, 1993, 366(6455): 588-590); the human c-myc promoter region (McWhinney C. and Leffak M., Nucleic Acids Res. 1990, 18(5): 1233-1242) and A34, a 36 bp consensus sequence derived from the human DNA-methyl transferase enzyme (dnmt) (Araujo F. D. et al., J. Biol. Chem., 1999, 274(14): 9335-9341). In addition four S/MAR sequences were selected with demonstrated activity in maintenance of episomes, mitotic stability and containing a transcriptional active regulatory domain for methylation. The selected anchoring elements were the 1.8 Kbp of the human IFN-γ gene (hIFN-γLarge) (Bode J. et al., Science, 1992, 255(5041): 195-7); the 0.7 Kpb minimal region of the same gene (hIFN-γShort) (Ramezani A. et al., Blood, 2003, 101(12): 4717-4724); the minimal region of 0.2K bp contained in the hamster dehydrofolate reductase gene (hDHFR) (Mesner L. D. et al., Proc. Natl. Acad. Sci. U.S.A., 2003, 100(6): 3281-3286) and finally a 0.4 Kbp region mapped in the mouse immunoglobulin kappa gene (mIgK) (Cockerill P. N. and Garrard W. T., Cell, 1986, 44(2): 273-282).

Figure 2:
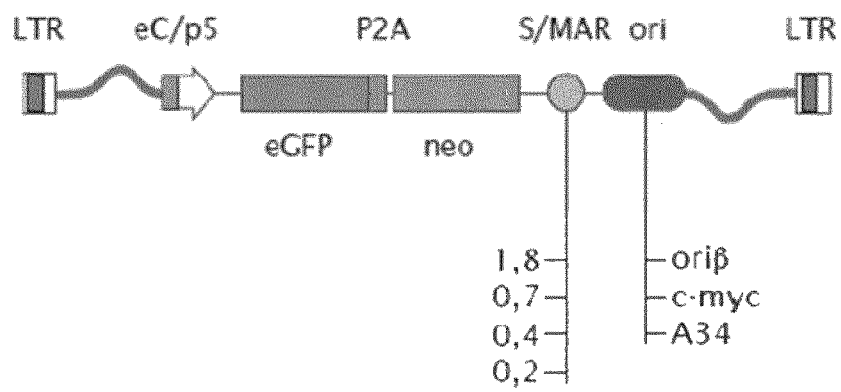
FIG. 2. Schematic design of LentiSome plasmids and vectors. (A) The basic elements contained in the shuttle pLS plasmids are depicted. Beside lentiviral elements maintained in the vectors, the transcriptional unit contains the CMV/p5 promoter (eC/p5) and the reporter cassettes, marked by a triangle and shadowed boxes respectively. The ori and S/MAR sequences are shown relative to the transcriptional unit at the 3'-half of the vector. S/MAR are named by their size in Kbp (see text for details).

To study whether or not the selected elements could be competent in a lentiviral format to promote persistence of the 1-/2-LTR episomes we generated self-inactivating lentiviruses with the mutation (D64N) in the pol gene that inactivates the viral integrase activity [Yañez et al, supra]. The plasmid named collectively pLS 1 (FIG. 2 and SEQ ID NO: 24) contains a transcriptional unit to address simply its maintenance upon transduction of the pLS-derived LentiSome™ along repeated cell divisions. The reporter cassette carries the eGFP/neoR ORFs separated by a poliovirus T2A CHYSEL sequence allowing to obtain results by either FACSorter or antibiotic selection respectively. The reporter cassette has been placed under the control of a weak but ubiquitous promoter encompassing the enhancer of the CMV and the p5 promoter from the early transcriptional unit of the adeno-associated virus 2 (eC/p5). To ensure the activation of the autonomously replicating sequences contained in the ori (ARS), both ori and S/MAR sequences were placed downstream of the transcription direction. The panel of constructs is shown in FIG. 2. The average size of the constructs was 9 Kbp ensuring further cloning of up to 4 Kbp cDNA. Each plasmid was used in combination with helper plasmids to generate lentivirus batches as described in Materials and Methods section.

In Silico Assessment of Structural Stability

To predict in silico the relative stability along the sequence of the pLS plasmids carrying ori/SMAR sequences we performed stress-induced DNA destabilization (SIDD) analysis. The readout of the study is a theoretical profile of the predicted energy needed to separate strands (represented by the ΔG°) along any nucleotide sequence, allowing determining specific regions in open conformation and with high propensity to separate strands (destabilized) as demonstrated in transcriptional termination sites and also for putative replication origin.

Figure 3:
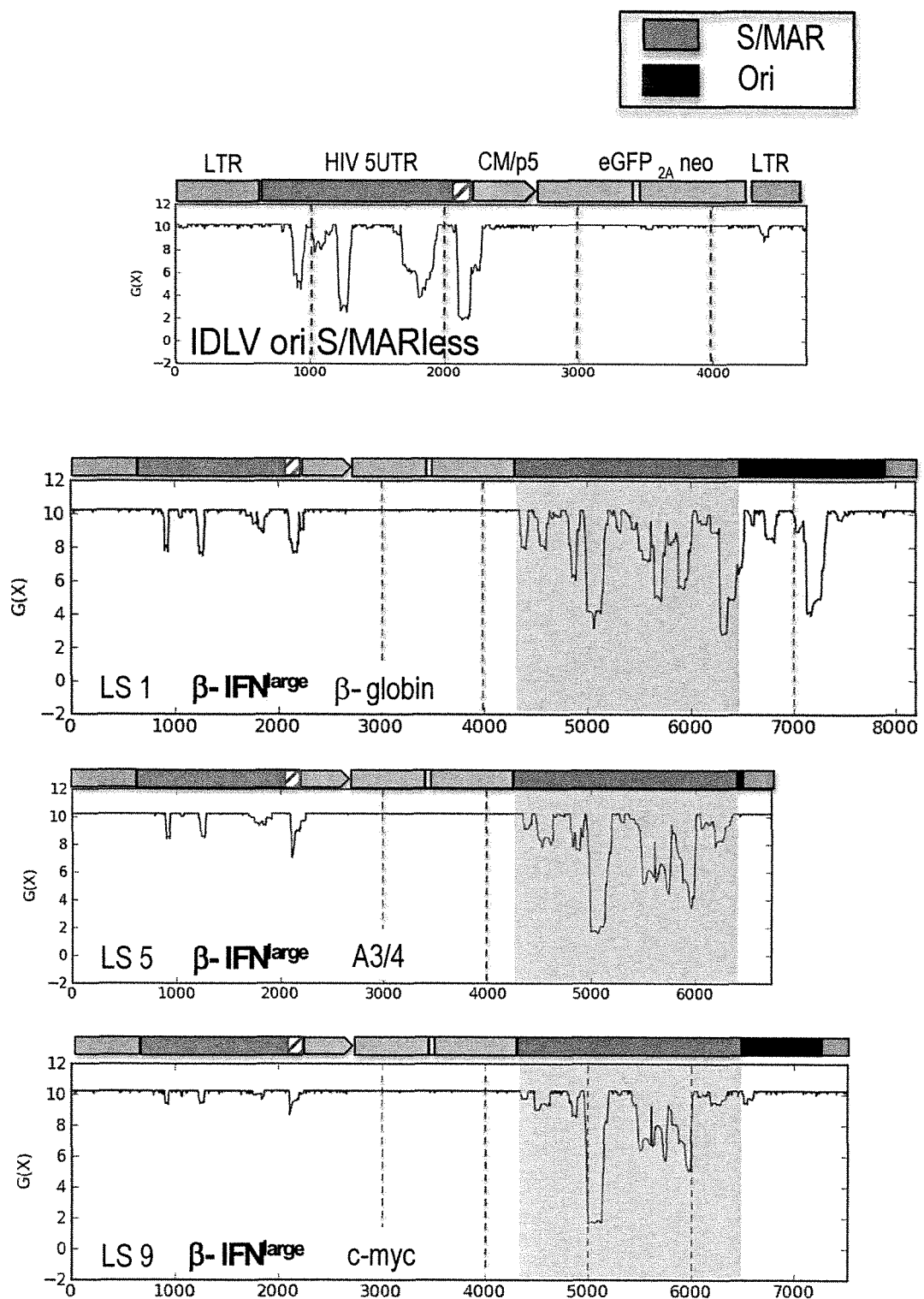
FIG. 3. Structural analysis of elements required for episomal replication. The figure shows the SIDD analysis run on the plasmids pLS representing the G(x) in Kcal/mol (see the text) along the sequence of the plasmid devoid of prokaryote sequences. Grey boxes delimit the elements contained in the shuttle lentiviral plasmids as indicated above the scheme of the control construct (Ori/SMAR less). The region corresponding to the S/MAR sequence is shaded with deep blue. Ori sequences are in black. The region with the minima G(X) in each construct has been highlighted with a shadow region.
Figure 3:
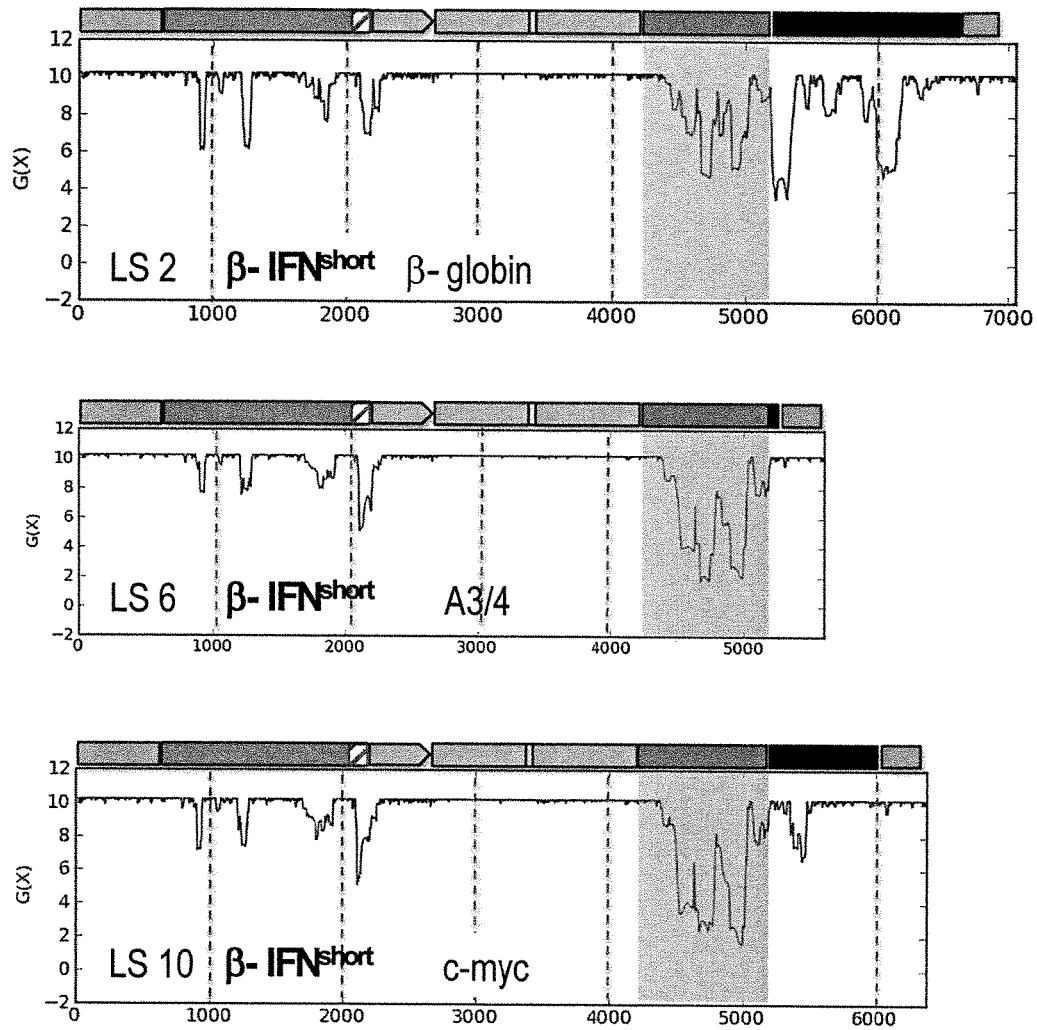
Figure 3:
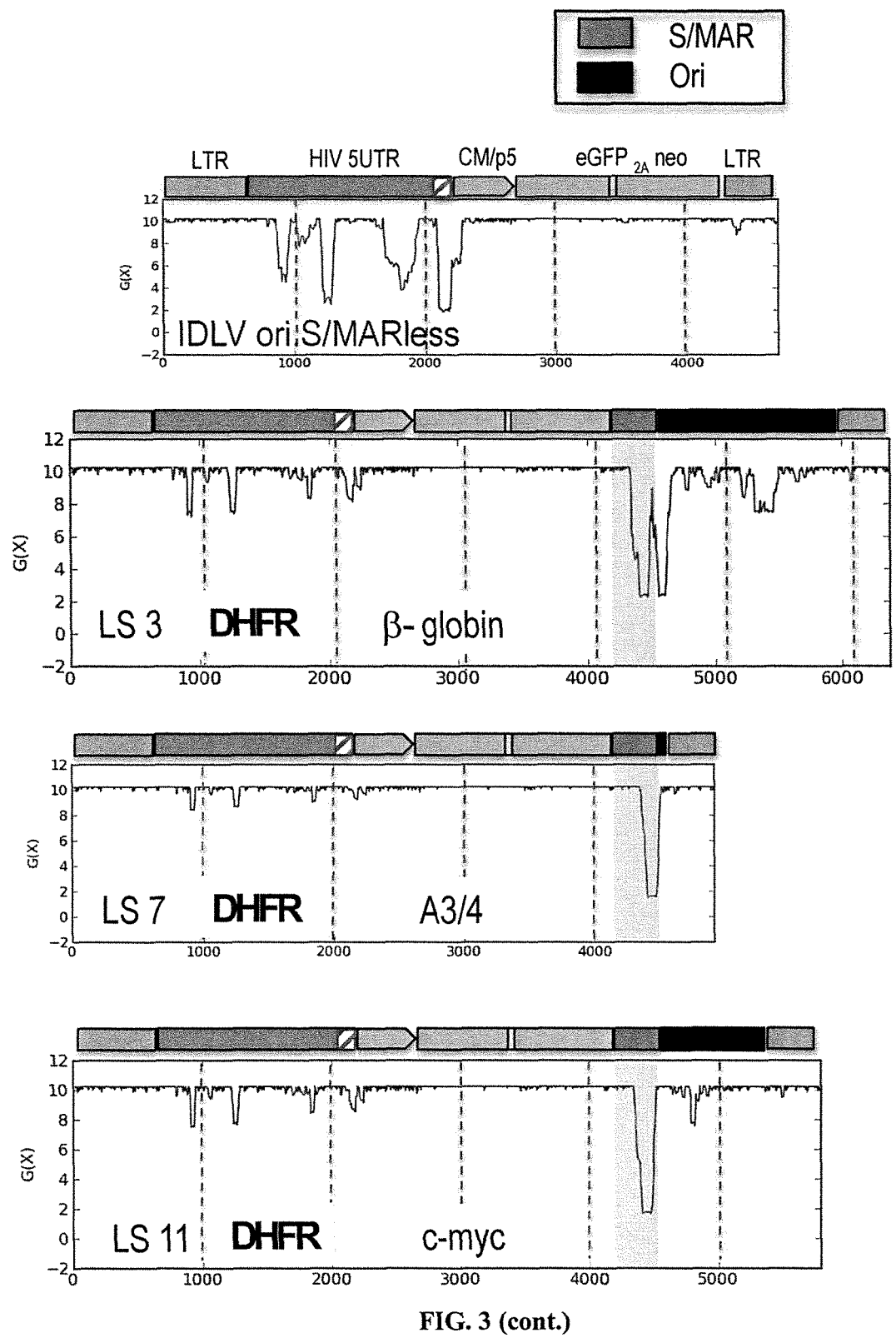
Figure 3:
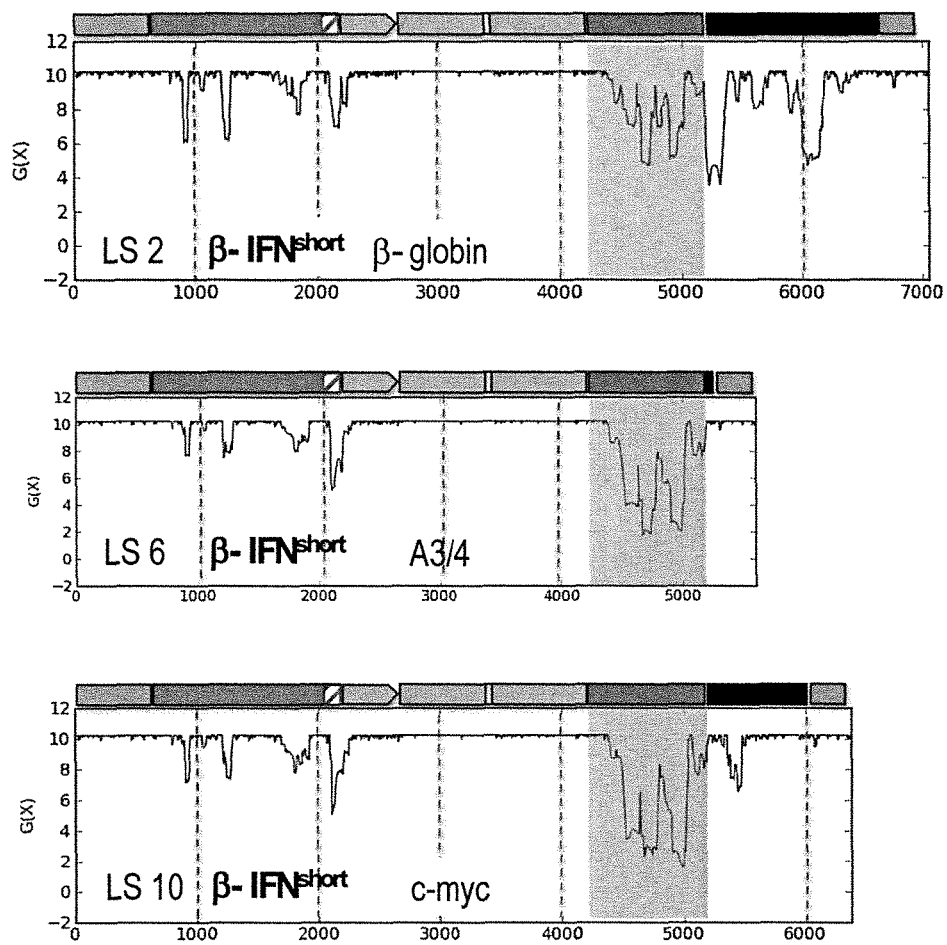

The data obtained with the 12 plasmids used along this study is shown in FIG. 3. The diagram represents the destabilization profiles for the sequence of each transfer lentiviral plasmid devoid of prokaryote sequences using the WebSIDD program (www.genomecenter.ucdavis.edu/benham). Above each profile are schemed the elements contained in each construct and the legend on the basic lentiviral structure is indicated above the scheme of the control construct (Ori/SMAR less). The region corresponding to the S/MAR sequence is shaded with deep blue. Ori sequences are in black. All the plasmids contain the highest probability of open structure, indicated as negative G(x) (in Kcal/mol) at the region spanning the S/MAR sequence (shadow region in the diagram). These data support the idea of an active open-region in all the S/MAR sequences cloned in the lentiviral backbone and are in agreement with the current description of the S/MAR sequences (Benham et al J. Mol. Biol. 274, 181-196 (1997).

Transduction and Stability of the Expression Kinetics

IDLV carrying the described ori/SMAR combinations were used to transduce at low MOI (2 T.U./cel) exponentially growing cultures of the human carcinoma cell line HEK293A cells. Cultures were maintained for five population doublings (PDs; 1 PD is equivalent to 18 hours in the culture conditions employed to twice passages/wk.) to allow for the establishment of episomes and after FACSorting purified eGFP+ cells. Afterward the cultures were maintained with or without G418 and scored every 8-10 PDs (6 to 7.5 days) for the presence of eGFP+ cells.

Figure 4:
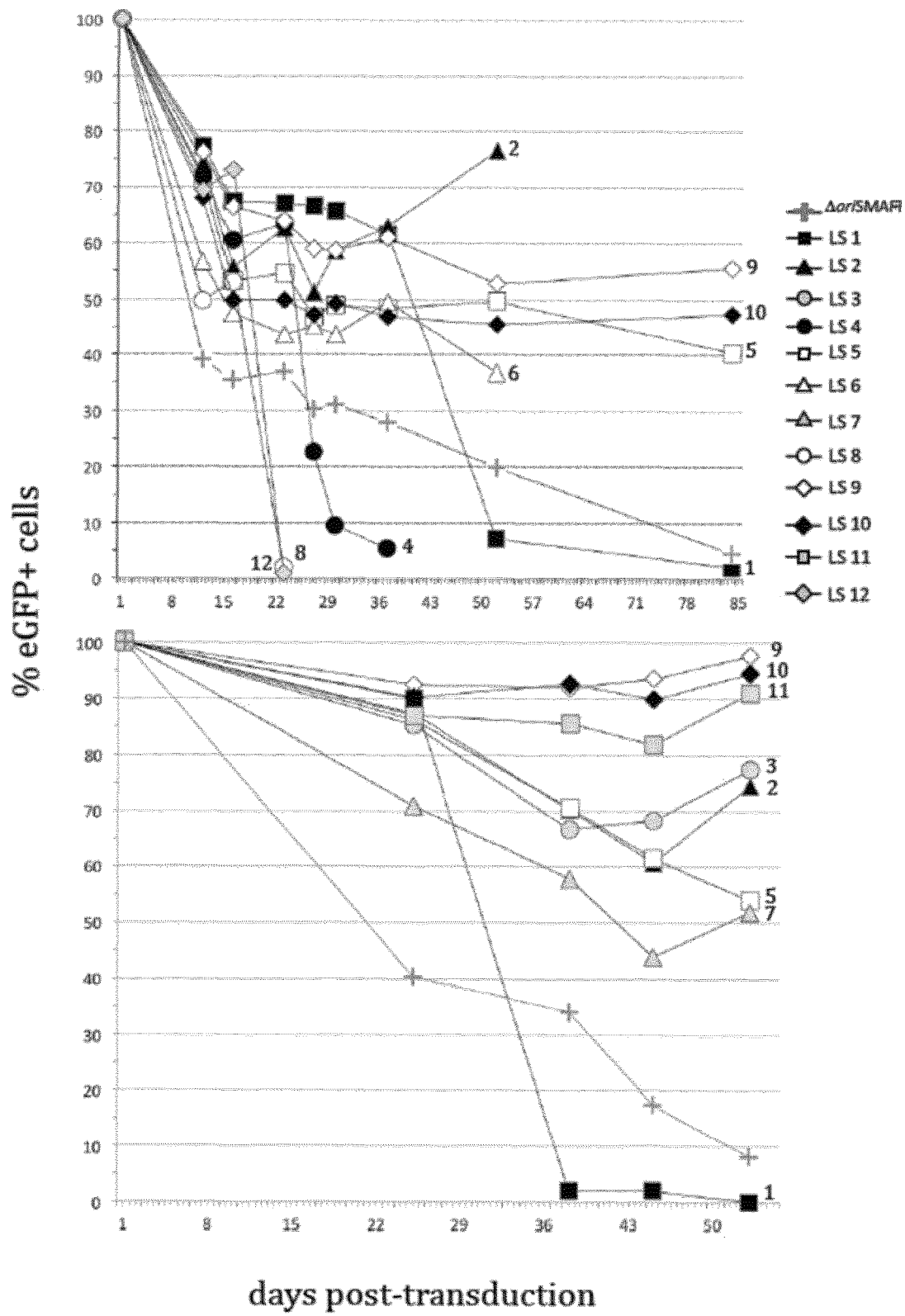
FIG. 4. Long-term expression of replicating LentiSomes in HEK293A cells after enrichment by FACsorter of eGFP expressing cells. Sets of LentiSomes were assayed in each panel. Cultures were maintained without selection upon establishment of the episomes (5 days post-transduction) and at the indicated time-points the number of eGFP+ cells were scored by FACS analysis. Refer to FIG. 2 to assignment of numbers and components combined in each case. Numerals in the graph correspond to LS number (see legend).

We first assessed persistence of LentiSome™ carrying each one of nine combinations of the aforementioned ori and either the S/MAR derived from the hIFNγ (LS 1, 2, 5, 6, 9 and 10) or from the mIgK (LS 4, 8 and 12) (FIG. 4, upper panel). After a period of 70 PDs in culture under no selective conditions (approximately 1.7 months after episomal establishment) the percentage of eGFP+ cells was variable on the basis of each transduced LentiSome™. Remarkably, most of the episomes containing the hIFNγ gene S/MAR (LS 2, 5, 6, 9 and 10) showed a stable propagation with cell divisions whereas those containing the mIgK small 0.4 Kbp S/MAR (LS 4, 8, 12) were not. It is also noticeable these LentiSome™ were repeatedly difficult to produce by reasons that have not been addressed yet. As expected, cultures maintained under selective conditions in the presence of G418 generate a homogeneous culture of cells resistant to the antibiotic the selection with G418 (data not shown).

Control values obtained with cells transduced with IDLV with neither ori or S/MAR sequences lost eGFP+ cells by the end time point of the assay as expected (cross symbols in FIG. 4). Cultures transduced with LS 5, 6 or 10 showed that functional episomes were left in 50% of the cells, whereas in cultures transduced with LS 1, 4, 8 or 12 the episomes persisted in less than 5% of the cell population at 70 PDs. Importantly, the episomes LS 2 and 9 were maintained and efficiently partitioned along the study as revealed by a high 70% of eGFP+ cells. Cultures transduced with LS 5, 9 and 10 were followed up longer until 120 PDs (three months after transduction) and almost equally results were obtained as the proportion of eGFP+ cells in the cultures were around 40-55% of the cell culture.

We performed a second trial with those LentiSomes™ that raised the better results in the former assay and included an additional set of lentiviruses. These contain a different element selected for its small size that fits one of the criteria mentioned in the experimental design. The novel element is the small 0.2 Kbp S/MAR of the hamster dehydrofolate reductase (DHFR). We then constructed and produced the LS 3, 7 and 11 in combination with the β-globin, A34 or c-myc ori respectively and followed the same approach comparing the set of LS 1, 2, 3, 5, 7, 9, 10 and 11, so discarding the LS containing the 0.4 Kbp S/MAR element.

In cultures transduced with LS 9, 10 and 11 at 70 PDs (54 days after establishment of episomes) the episomes persisted in 90% of the cells, suggesting an efficient replication, firing and segregation (FIG. 4, bottom panel) and in particular, the persistence achieved when the c-myc ori sequences were combined with all the S/MAR sequences tested. Table 1 shows a resume of the data represented in FIG. 4.

TABLE 1

End-point data from long-term expression of replicating LentiSomes in HEK293A.

| | | | % EGFP+ cells (*) | | | | |
|---|---|---|---|---|---|---|---|
| | | | days post-transduction | | | | |
| | | | | 52 | 84 (**) | | |
| | | | | population doublings | | | avg |
| LS | Ori | | S/MAR | 69 | | 108 | (***) |
| 1 | b-globin | 1.8 | hIFN-g$^{Large}$ | 7.1 | 0 | 0 | 3.6 |
| 2 | | 0.7 | hIFN-g$^{Short}$ | 76.4 | 74.4 | | 75.4 |
| 3 | | 0.2 | haDHFR | 79.1 | 77.4 | | 78.3 |
| 4 | | 0.4 | mIgK | 5.5 | | | 5.5 |
| 5 | A3/4 | 1.8 | hIFN-g$^{Large}$ | 49.6 | 54 | 40.3 | 51.8 |
| 6 | | 0.7 | hIFN-g$^{Short}$ | 36.8 | | | 36.8 |
| 7 | | 0.2 | haDHFR | | 51.8 | | 51.8 |
| 8 | | 0.4 | mIgK | 0 | | 0 | 0 |
| 9 | hc-myc | 1.8 | hIFN-g$^{Large}$ | 52.7 | 97.7 | 84.9 | 55.5 | 78.4 |
| 10 | | 0.7 | hIFN-g$^{Short}$ | 45.4 | 94.6 | 84.9 | 47.3 | 75.0 |
| 11 | | 0.2 | haDHFR | 91 | 86.8 | 88.4 | 88.7 |
| 12 | | 0.4 | mIgK | 0 | | 0 | 0 |

(*) percentage of eGFP+ cells at the end of the assay (dpt)
(**) data at 108 PD correspond to the end point value of the first column assay
(***) only data from assays at 69 PD have been considered for this calculation Conclusions From the previous of experiments it can be concluded (i) the feasibility of our approach in the lentiviral backbone and (ii) that significantly in the lentiviral context a trial and error strategy must be followed as no all combinations are either equally well tolerated or theoretically predicted.

Apparently there is no predictive general rule to find the optimal combination of elements to be included in the lentiviral backbone that allows to efficient persistence. However there are some sequences showing features worth to remark i.e. LS containing the mIgK 0.4 Kbp S/MAR do not seems competent to segregation regardless the ori sequence combined with; whereas the ori in the human c-myc and β-globin genes seem to persist efficiently regardless the accompanying S/MAR sequence. Noticeable, the set of LentiSome™ bearing the human c-myc ori sequence persisted whichever the tested S/MAR sequences were placed together, a fact opposite compared to results obtained with S/MAR mIgK.

In conclusion, and in spite of the well characterized ori and S/MAR sequences when delivered by DNA viruses, plasmids and minicircle (Nehlsen K. et al., Gene Therapy and Molecular Biology, 2006, 10: 233) we have shown that the genetic features imposed by the lentiviral replicative intermediates precludes any prediction concerning persistence in dividing cells.

Example 2: Genetic Analysis of LentiSome™ in Transduced Cells

Analysis of the Extra-Chromosome State of the Lenti-Somes™ in Transduced Cells

It is currently well established that the function of mammalian ori relies on epigenetic principles, such as the presence of bound transcription factors, chromatin structure, or nuclear localization. Less is known about the requirements for the S/MAR sequences to be functional besides the need for anchorage proteins.

As far as we know there are no data addressing the state of the 1-/2-LTR off-products during classical lentivirus or IDLV transduction or infection and then we were wondering whether ori/SMAR sequences might be acting physiologically when present in the lentiviral genetic structures. We first addressed if LS deliver forms integrate or to what extent and if all combinations are equally efficient. We used a set of techniques aimed at uncover this point according with standard procedure described in the literature (see Nehlsen K. et al., supra).

Southern Blot Studies

Figure 5:
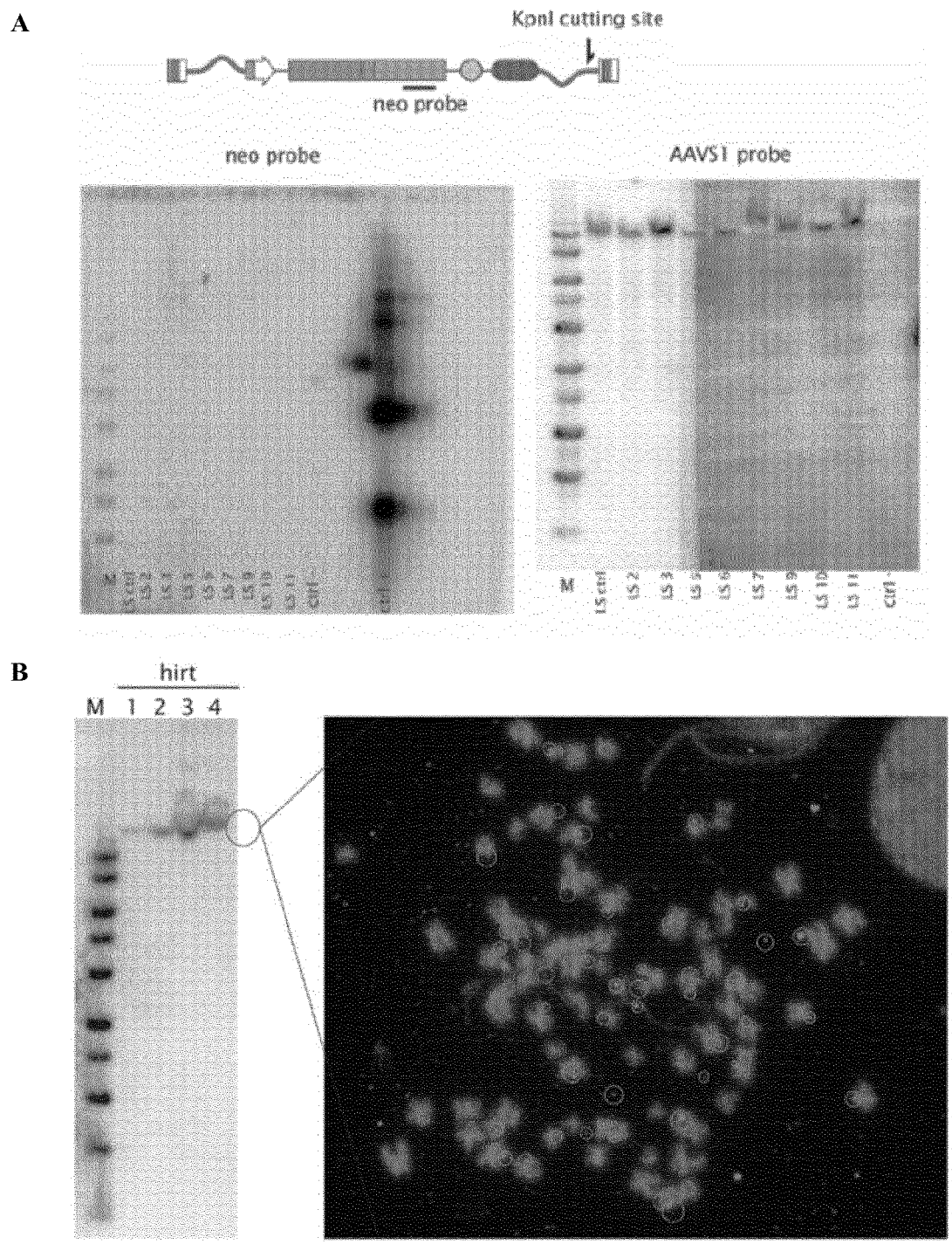
FIG. 5. Southern blot-analysis for episomally replicating LentiSomes in HEK293A cells. (A) Representative image obtained with genomic DNA from the indicated LS-transduced cells hybridized with a specific neo probe (left) and a probe to the AAVS1 locus. (B) Southern blot on Hirt's extracts at 5 days post-transduction with the indicated clones. The FISH image on the right probed with the pLS (white circles) shows the abundant number of plasmids and intermediates in cells of transduced with LS 5. Southern blot under such conditions is sensitive enough to develop the positive bands.

Both genomic and low molecular weight DNA (Hirt's extract) was purified from transduced cells with a set of LS after continued cultivation (>70 PDs) and samples were studied first by Southern blot. Genomic DNA digested with enzyme cutting once in the 3' end of all LS was blotted and hybridized with a specific neo probe directed to the endogenous locus AAVS1 that is represented three times per cell HEK293K. When filters were hybridized with the specific neo probe (FIG. 5A, left) no specific signal was obtained by this technique in none of the samples studied. The AAVS1 probe hybridized in all samples revealing a maximum of 2-fold variation in the cell equivalents loaded per lane (FIG. 5A, right). The sensitivity of neo probe under the experimental conditions was 10-fold higher that the AAVS1 probe that detects 3 copies/cell and in each lane equals to 1 million cells equivalents, then it can be concluded that numbers of integrated copies of the LentiSomes were lower than 0.3/cell. When Hirt's extracts were studied by Southern blot, similar negative results were obtained though in this case a lower sensitivity was achieved and limits to detection of more than 50 copies per cell. Indeed when high number of copies was present, i.e. at the end of the episomal establishment, Hirt's extract from cultures transduced with LS 1, 2, 5 and 10 showed a specific band in the Southern blot (FIG. 5B left). Importantly, FISH studies of those cultures at that time-point showed abundant number of spots in all cells scored, a data that correlates with their detection by Southern blot (FIG. 5B right).

Collectively these results might be explained if Lenti-Some persist in low numbers in culture, and support the inability to detect them by Southern blot. Indeed, data from other authors with the episomal minicircle plasmid pEPI (Nehlsen, Broll and Bode, 2006) indicate that 10-15 copies are maintained in CHO cultures after continued cultivation without selection, and detected only by Southern blot at early time after episomal establishment as is our case.

PCR Analysis

Despite the information provided by Southern blot is necessary to detect specific location of probed sequences the technique is poorly informative when low copy numbers of a sequence in a fraction of cells are being searched for. As episomes are likely present at low copy numbers and likely in a fraction of the cells, the IDLV sequences in cultures with persistent phenotype were further characterized by qPCR.

Figure 6:
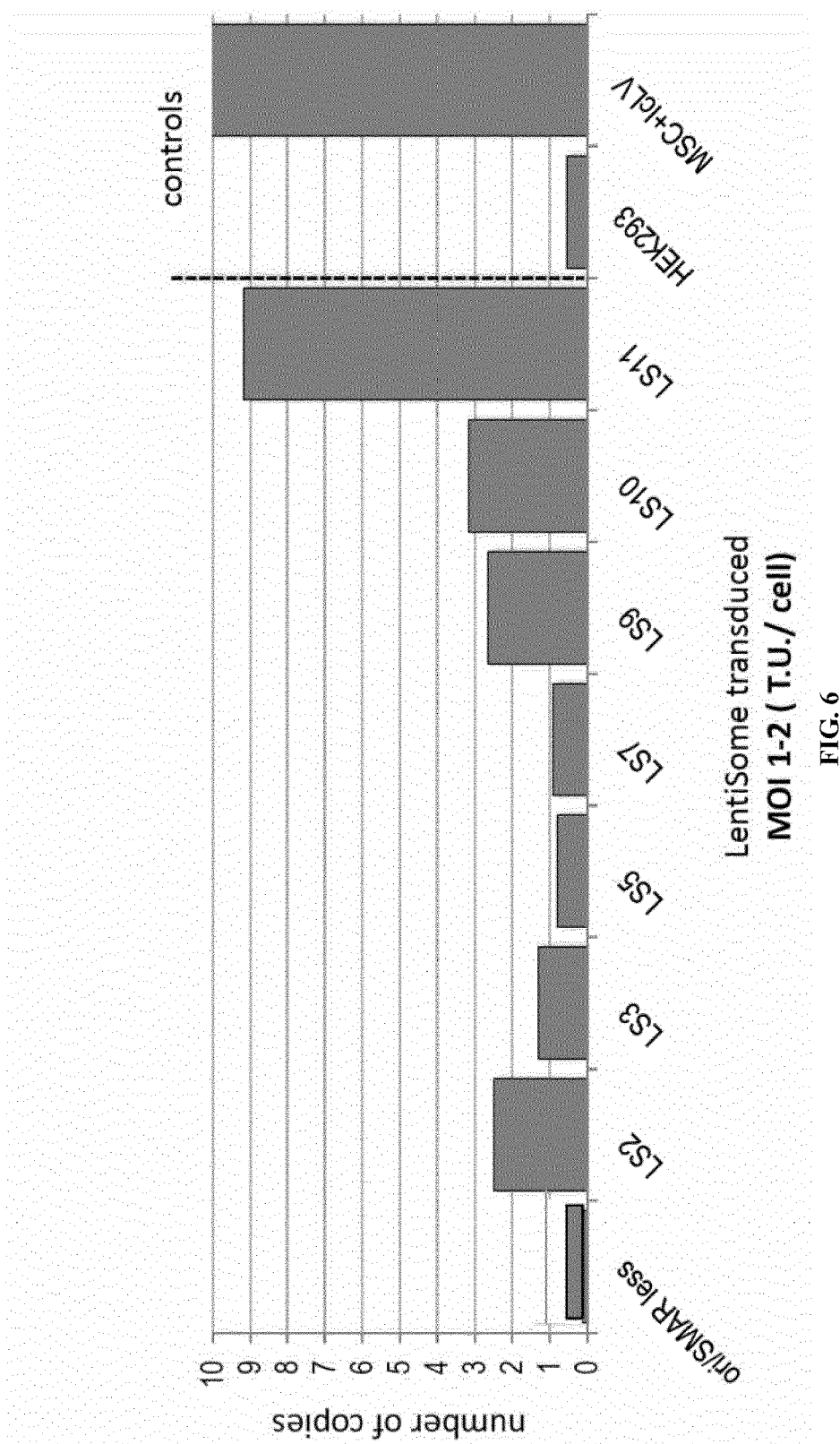
FIG. 6. PCR analysis of episomal replicating LentiSomes. Genomic DNA of eGFP+ cultures at 69 population doublings after transduction with the indicated LS were used to perform 2-LTR qPCR using specific primers. Copy number of 2LTR were detected by qPCR of genomic DNA and normalized relative to the albumin gene, which is single-copy gene in HEK293A cells. Background levels were obtained with samples from untransduced parental cells (HEK293A) and positive PCR control was obtained with samples transduced with integration competent lentivirus. The numbers of cells analyzed for each culture were as average $10^4$. A representative experiment out of three independent is represented, and values are average of three replicas in the reaction.

Highly sensitive quantitative qPCR was performed on genomic DNA samples to detect relative abundance 2-LTR episomal forms sequences in cultures transduced with LS 2, 3, 5, 7, 9, 10 and 11 left in culture at 69PDs and compared to signal obtained with parental HEK293A DNA either untransduced or transduced with an integrative lentivirus or with a IDLV without ori and S/MAR sequences. Cell equivalents were normalized by specific qPCR to detect the single copy albumin gene. FIG. 6 shows that values obtained by qPCR using HIV LTRs primers were between 1 copies/cell (LS 3, 5, 7), 2-3 copies/cell (LS 2, 9 and 10) or more than 9 copies/cell (LS11). Such numbers supports the idea that only few episomal copies were present in the cultures. Values obtained with cells transduced with the IDLV-ori/SMAR less were below the detection limits and are considered equal to those obtained with control untransduced cells (FIG. 6, HEK293 lane) and thus fall into background values.

In summary, data from the qPCR analysis indicates that frequency of maintenance of the episomal forms specifically detected with the 2-LTR PCR is low and variable between the different transduced cultures upon stabilization.

Extra-Chromosomal State of the LentiSome

Figure 7:
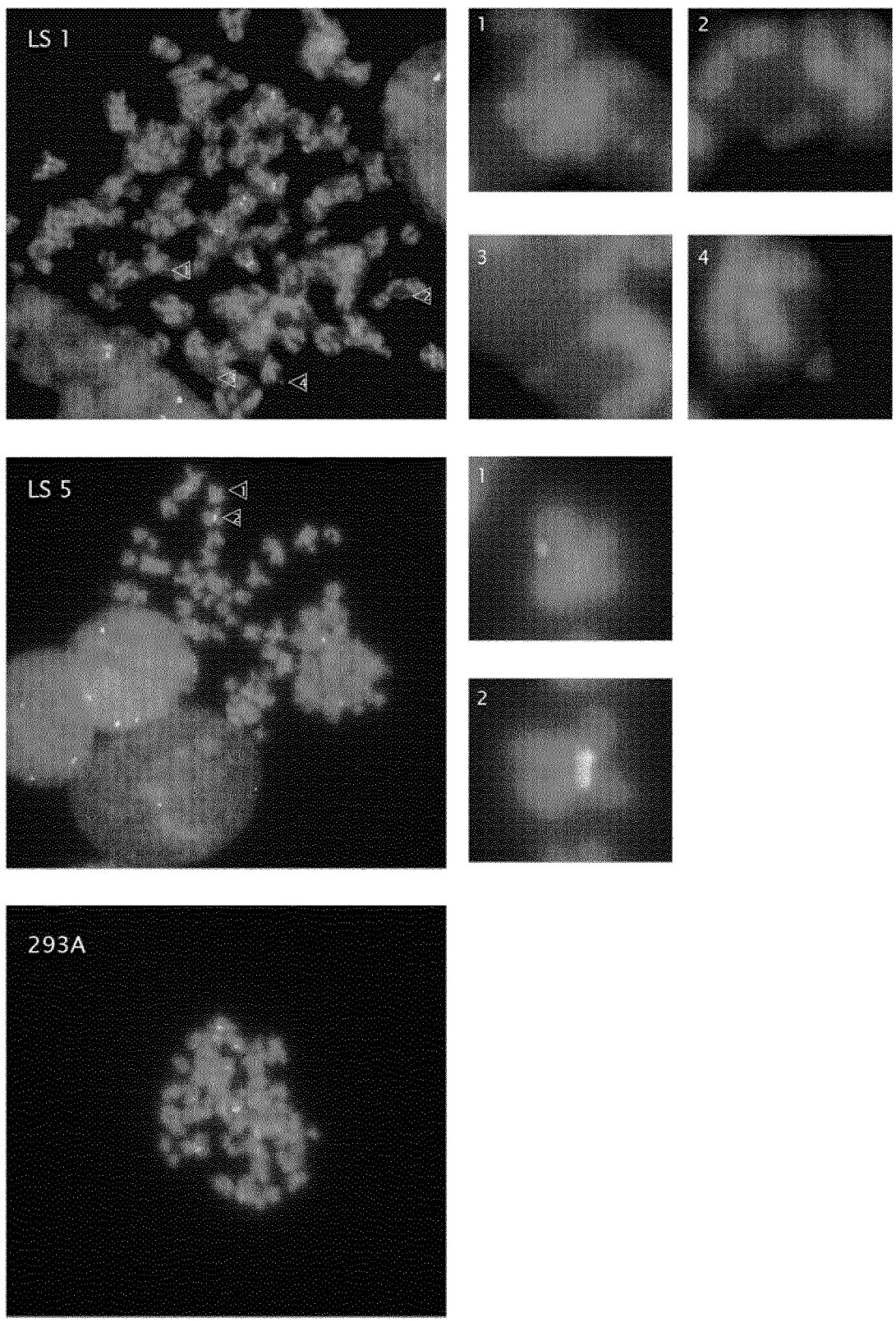
FIG. 7. FISH analysis of LS transduced HEK293A cells at 54 days pot-transduction. Metaphase spreads of representative field of eGFP+ cells with episomally replicating LentiSomes. Most double white spots are signals of positive centromere control probe 4q113.3, whereas LS sequences are detected as non-double dots (Enlarged views are indicated by numbers).
Figure 7:
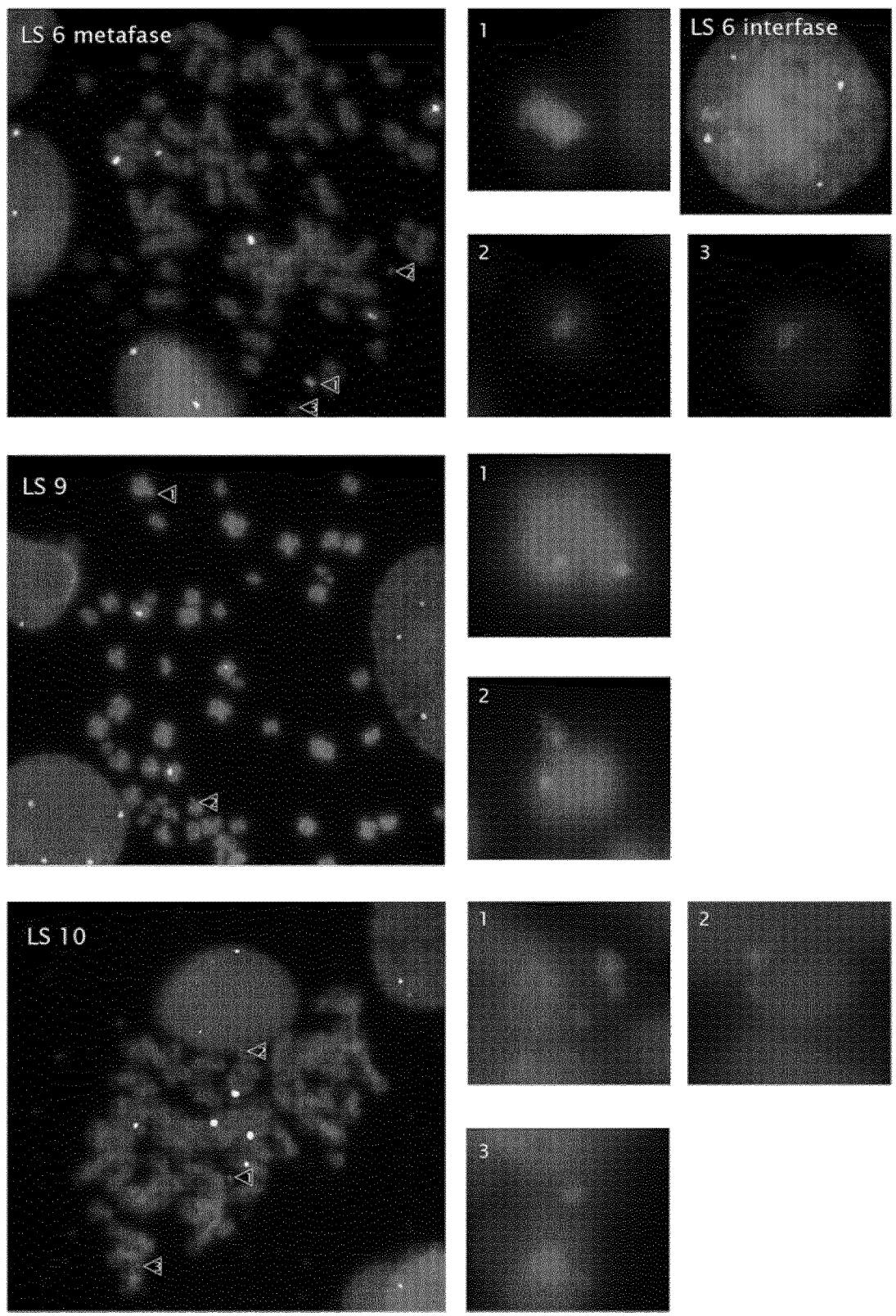

As suggested by the previous data, the copy number of LS-type vectors is low but certain combinations are stably maintained during cell divisions whereas other might no. We have performed FISH analysis as a definite proof to demonstrate the association with chromosomes of the LS derived-intermediates. FIG. 7 shows metaphase spreads of cells transduced with LS 5, 6, 9, 10 or 11 at 70 PDs. As shown in cells transduced with LS 5, 6, 10 or 11 we consistently found sharp fluorescent sports in association with metaphase chromosomes but not duplicated signals at identical positions in the chromosome arms. Although this is also true for the majority of the cells transduced with the LS 9 there are rare exceptions (see insert in FIG. 7) where intense doublets on both chromosome arms are observed, indicative of integration events of the circular constructs. Such a result could agree certain sets of data obtained by conventional qPCR and PCR (FIG. 6) whereas not others.

The apparent discrepancy supports the rationale exposed by other authors when comparing results obtained with these different techniques. Indeed, FISH analysis correlates well with data generated by qPCR and supports the concept that the former should be the procedure of choice. Therefore, due to inconsistencies along the results obtained with different techniques, we agreed arguments of other authors emphasizing data from FISH-visualization of transgenes in metaphase spreads. Yet single intense signal indicating the typical extrachromosome copies in contrast with doublets in both chromatids happening upon integration.

Conclusions

We have demonstrated that it is possible to transfer autonomous replication and segregation competences to lentiviral retrotranscription off-products (1-/2-LTR) by insertion of ori and S/MAR sequences in the viral genome. The main factors that contribute to the function of the invention are likely among the nuclear trafficking of the off-products; the mammalian nature of the sequences studied; and the minimal interference with the cell physiology upon transduction with lentiviral vectors.

We have also conserved the relative position of the transcriptional unit (reporter) placed upstream to the replication regulatory unit (ori/SMAR) as of major concern in literature. It is remarkable that unpredictably results were obtained, as several but not all combinations are equally effective and few are inefficient in this context, like the 0.4 Kbp S/MAR from mIgK despite the well characterization of the element in other non-viral systems, such as approaches with plasmids and minicircles. Thus, trial and error approach is required to demonstrate fully functionality of the episomal maintenance with no detectable integrations in the context of lentiviral genetics.

Such novel lentiviral-derived episomal vectors (LentiSome) can take advantage of the state of the art of the conventional lentivectors in pre-clinical and clinical trials and become a vector of choice for safer next generation gene therapy approaches.

The invention claimed is:

1. A polynucleotide comprising
   (i) a first long terminal repeat derived from a lentivirus,
   (ii) an eukaryotic origin of replication selected from the group consisting of the origins of replication having the sequence of SEQ ID NO: 1, SEQ ID NO: 2, SEQ ID NO: 3 and a functionally equivalent variant thereof, wherein the functionally equivalent variant has at least 70% of sequence identity across the whole length of the sequence with the sequences SEQ ID NO; 1, SEQ ID NO: 2 or SEQ ID NO: 3,
   (iii) a scaffold/matrix attachment region selected from the group consisting of the scaffold/matrix attachment regions having the sequence of SEQ ID NO: 4, SEQ ID NO: 5, SEQ ID NO: 6 and a functionally equivalent variant thereof, wherein the functionally equivalent variant has at least 70% of sequence identity across the whole length of the sequence with the sequences SEQ ID NO; 4, SEQ ID NO: 5 or SEQ ID NO: 6, and
   (iv) a second long terminal repeat derived from said lentivirus, wherein said eukaryotic origin of replication and said scaffold/matrix attachment region are located between said first and second long terminal repeats.

2. The polynucleotide according to claim 1, wherein the scaffold/matrix attachment region is located at a 5' position with respect to the eukaryotic origin of replication.

3. The polynucleotide according to claim 1, wherein the first long terminal repeat comprises SEQ ID NO: 7 and the second long terminal repeat comprises SEQ ID NO: 8.

4. The polynucleotide according to claim 1, wherein the second long terminal repeat comprises a self-inactivating mutation.

5. The polynucleotide according to claim 1, further comprising a polynucleotide sequence selected from the group consisting of:

a multiple cloning site;
at least a first polynucleotide of interest operatively linked to a promoter, wherein the promoter is located at a 5' position with respect to the scaffold/matrix attachment region and with respect to the eukaryotic origin of replication, and at a 3' position with respect to the first long terminal repeat; and the polynucleotide of interest is located at a 5' position or at a 3' position with respect to the scaffold/matrix attachment region and at a 5' position or at a 3' position with respect to the eukaryotic origin of replication; and
combinations thereof.

6. The polynucleotide according to claim 5, further comprising an enhancer region operatively linked to the promoter.

7. The polynucleotide according to claim 6, wherein the promoter comprises SEQ ID NO: 9, the enhancer region comprises SEQ ID NO: 10, and the polynucleotide of interest encodes neomycin, green fluorescent protein, or a combination thereof.

8. The polynucleotide according to claim 5, further comprising a second polynucleotide of interest operatively linked to the first polynucleotide of interest by a sequence encoding a cotranslational self-processing sequence.

9. The polynucleotide according to claim 8, wherein the sequence encoding the cotranslational self-processing sequence comprises SEQ ID NO: 11.

10. The polynucleotide according to claim 1, further comprising a primer binding site sequence derived from a lentivirus, wherein said primer binding site sequence is located at a 3' position with respect to the first long terminal repeat and at a 5' position with respect to both the origin of replication and the scaffold/matrix attachment region, and further wherein if the polynucleotide further comprises a polynucleotide sequence selected from the group consisting of:

a multiple cloning site, a polynucleotide of interest operatively linked to a promoter, wherein the promoter is located at a 5' position with respect to the scaffold/matrix attachment region and with respect to the origin of replication, and at a 3' position with respect to the first long terminal repeat, and the polynucleotide of interest is located at a 5' position or at a 3' position with respect to the scaffold/matrix attachment region and at a 5' position or at a 3' position with respect to the origin of replication; and combinations thereof, then the primer binding site is located at a 5' position with respect to said polynucleotide sequence.

11. The polynucleotide according to claim 1, further comprising a packaging signal sequence derived from a lentivirus located between the first long terminal repeat and the second long terminal repeat.

12. The polynucleotide according to claim 10, further comprising a packaging signal sequence derived from a lentivirus located between the first terminal repeat and the second terminal repeat, wherein the packaging signal sequence comprises SEQ ID NO: 13, and further wherein the primer binding site sequence comprises SEQ ID NO: 12.

13. The polynucleotide according to claim 1, further comprising a Rev response element derived from a lentivirus located between the first long terminal repeat and the second long terminal repeat.

14. The polynucleotide according to any claim 1, further comprising a central polypurine tract derived from a lentivirus, wherein said central polypurine tract is located at a 3' position with respect to the first long terminal repeat and at a 5' position with respect to both the origin of replication and the scaffold/matrix attachment region, and further wherein if the polynucleotide further comprises a polynucleotide sequence selected from:

a multiple cloning site, a polynucleotide of interest operatively linked to a promoter, wherein the promoter is located at a 5' position with respect to the scaffold/matrix attachment region and with respect to the origin of replication and at a 3' position with respect to the first long terminal repeat, and the polynucleotide of interest is located at a 5' position or at a 3' position with respect to the scaffold/matrix attachment region and at a 5' position or at a 3' position with respect to the origin of replication, and combinations thereof, then the central polypurine tract is located at a 5' position with respect to said polynucleotide sequence.

15. The polynucleotide according to claim 1, further comprising a prokaryotic origin of replication and a selection marker.

16. The polynucleotide according to claim 15, wherein the central polypurine tract comprises SEQ ID NO: 15, the prokaryotic origin of replication comprises SEQ ID NO: 16, and the selection marker is ampicillin.

17. The polynucleotide according to claim 1, wherein said polynucleotide is within a vector and/or within a cell.

18. The polynucleotide according to claim 1, wherein said polynucleotide is present in a recombinant lentivirus, and further wherein said recombinant lentivirus comprises a lentiviral integrase comprising a mutation that causes said integrase to be unable to catalyze the integration of the viral genome into a cell genome.

19. A stable cell population which can express a polynucleotide of interest comprising the polynucleotide of claim 1, wherein said polynucleotide comprises a polynucleotide of interest operatively linked to a promoter, wherein:

the promoter is located at a 5' position with respect to both the scaffold/matrix attachment region and the origin of replication and at a 3' position with respect to the first long terminal repeat; and the polynucleotide of interest is located at a 5' position or at a 3' position with respect to the scaffold/matrix attachment region and at a 5' position or at a 3' position with respect to the origin of replication.

20. An in vitro method for generating a recombinant lentivirus according to claim 1, the method comprising:

(i) contacting a eukaryotic cell with a polynucleotide according to claim 1 or with a vector comprising a polynucleotide according to claim 1, wherein the eukaryotic cell expresses a lentiviral gag protein, a lentiviral poi protein, a lentiviral rev protein, and a viral envelope protein under conditions adequate for entry of the polynucleotide or the vector into said cell; and (ii) maintaining the eukaryotic cell under conditions adequate for assembly of the recombinant lentivirus.

* * * * *

UNITED STATES PATENT AND TRADEMARK OFFICE
CERTIFICATE OF CORRECTION

PATENT NO. : 10,294,492 B2
APPLICATION NO. : 15/100110
DATED : May 21, 2019
INVENTOR(S) : Juan Carlos Ramírez Martínez, Raúl Torres Ruiz and Aida García Torralba Page 1 of 1

It is certified that error appears in the above-identified patent and that said Letters Patent is hereby corrected as shown below:

On the Title Page

Column 1, item (71), Line 2:
Replace "Cariovasculares"
With –"Cardiovasculares–

Signed and Sealed this
Ninth Day of July, 2019

Andrei Iancu
*Director of the United States Patent and Trademark Office*

SEQUENCE LISTING

<160> NUMBER OF SEQ ID NOS: 25

<210> SEQ ID NO 1
<211> LENGTH: 1484
<212> TYPE: DNA
<213> ORGANISM: Homo sapiens

<400> SEQUENCE: 1

```
gaggatccag tttcttttgg ttaacctaaa ttttatttca ttttattgtt ttattttatt      60
ttattttatt ttattttgtg taatcgtagt ttcagagtgt tagagctgaa aggaagaagt     120
aggagaaaca tgcaaagtaa aagtataaca ctttccttac taaaccgaca tgggtttcca     180
ggtaggggca gaacactgag accctacgct gacctcataa atgcttgcta cctttgctgt     240
tttaattaca tcttttaata gcaggaagca gaactctgca cttcaaaagt ttttcctcac     300
ctgaggagtt aatttagtac aaggggaaaa agtacagggg gatgggagaa aggcgatcac     360
gttgggaagc tatagagaaa gaagagtaaa ttttagtaaa ggaggtttaa acaaacaaaa     420
tataaagaga aataggaact tgaatcaagg aaatgatttt aaaacgcagt attcttagtg     480
gactagagga aaaaaataat ctgagccaag tagaagacct tttcccctcc taccoctact     540
```

```
ttctaagtca cagaggcttt tgttcccc agacactctt gcagattagt ccaggcagaa      600
acagttagat gtccccagtt aacctcctat ttgacaccac tgattacccc attgatagtc      660
acactttggg ttgtaagtga cttttttattt atttgtattt ttgactgcat taagaggtct      720 ctagttttt atctcttgtt tcccaaaacc taataagtaa ctaatgcaca gagcacattg      780
atttgtattt attctatttt tagacataat ttattagcat gcatgagcaa attaagaaaa      840
acaacaacaa atgaatgcat atatatgtat atgtatgtgt gtatatatac acacatatat      900
atatatattt tttcttttct taccagaagg ttttaatcca aataaggaga agatatgctt      960
agaaccgagg tagagttttc atccattctg tcctgtaagt attttgcata ttctggagac     1020
gcaggaagag atccatctac atatcccaaa gctgaattat ggtagacaaa actcttccac     1080
ttttagtgca tcaacttctt atttgtgtaa taagaaaatt gggaaaacga tcttcaatat     1140
gcttaccaag ctgtgattcc aaatattacg taaatacact tgcaaaggag gatgtttta      1200 gtagcaattg tactgatggt atggggccaa gagatatatc ttagagggag ggctgagggt     1260
ttgaagtcca actcctaagc cagtgccaga agagccaagg acaggtacgg ctgtcatcac     1320
ttagacctca ccctgtggag ccacacccta gggttggcca atctactccc aggagcaggg     1380
agggcaggag ccagggctgg gcataaaagt cagggcagag ccatctattg cttacatttg     1440
cttctgacac aactgtgttc actagcaacc tcaaacagac acca                      1484

<210> SEQ ID NO 2
<211> LENGTH: 36
<212> TYPE: DNA
<213> ORGANISM: Homo sapiens

<400> SEQUENCE: 2
cctcaaatgg tctccaattt tcctttggca aattcc                                36

<210> SEQ ID NO 3
<211> LENGTH: 810
<212> TYPE: DNA
<213> ORGANISM: Homo sapiens

<400> SEQUENCE: 3
tggctgcctt ccaggcatta atttcctagt tcactgactc acaattttt ctgaatacta       60 gtgaaagtgc actgtatgta acccgcaaac gtgtattcac attttattta cgcttcgact     120
cagctagttg cccagcccca cacatgattt gtttgctccc tgaaatgatc tatatttaat     180
atataatgta tattccctcg ggatttttta ttttgtgtta ttccacggca tgaaaaacaa     240
aaaacattct tctcatcctt ggtccctcac ccaaaggcat tttaagtaaa ctttctctc      300 cctccaccac ctccaaaaga gaaacaatt cgggggaaag gggtgtgtgt atagcatgta      360
cgctgttcaa gatgggttat tacccgttga gtttgcagct cagcgttcaa gtgttaagtg     420
aatatagtag cttccaaatc cgatgcactg cacaattcag ctttaaggat tgcaaattac     480
tcctgcctcc aggcctttgc cgcaaacgcg gggagcaacc aatcgctatg ctggattttg     540
ctgcaaagcg tctttccctc cgcccctct ctgggcagca ccgcgttca ggtttgcgaa      600 agtaaagtaa gtgtgccctc tactggcagc agagatcatc gcgcctggat gtcaacgagg     660 gcggggtca ggtggggca ggagcaggag cgtccgaggt gcaaggtttc cagcggggga      720
aggacaggcg gttccttaaa acaagtttcc agccacctcc ttgttattct ttcaggttgg     780
ctgcagaagg tccgaagaaa gaggagttac                                      810
```

<210> SEQ ID NO 4
<211> LENGTH: 1988
<212> TYPE: DNA
<213> ORGANISM: Homo sapiens

<400> SEQUENCE: 4

```
cgctatcaag atatttaaag aaaaaaaaat tgtatcaact ttctacaatc tctttcagaa      60
gacagaagca gagggaatac ttcctaaatc attcaactag gccagcatta ccttaatacc     120
ggaactagaa aatgacatta caagaaaaga aaacaacaga ccaatatctc tcatgaacaa     180
agatacaaac attttcaaca aaatattagc aaaagaatc caagaatgta tcaaaaaata     240
tacaccacaa ccaagtagaa tttattccag atatgtaagg gtggttcaac gtttgaaaat     300
caattaacgt aatttgtccc atcaacaggt taaagaagaa aatcacatgg tcatattgat     360
agacacagaa aaagcatttg acaaaattta acacccattc atgatgcaat ctctcagtaa     420
actaggaata gaggaaaact tcctcagctt gaatgtacct tcctctcaat tttgctatga     480
acctgaaact cctcttaaaa aataaagttt ttcatttaaa aagaaaacaa aaaacatgga     540
ggagcgttga tgtatctcat tttagaccaa tcagctatgg atagttaggc gacagcacag     600
atagctgctg tacttctgtt tctggcaatg ttccagacta catttaaaaa attttttaatt     660
atagacttgt acttaatgtt caagaaaaat atgaaaatga ctttgccgtg ttaatgctac     720
tcttttttaa aaaaaactaa agttcaaact ttatttatat ttcattagtt ttttagctac     780
tgttcttttt ctgttctggg atctcattca gaatgccaca ttacatataa ttctcatgtc     840
tccttgggtt cctcttagtt ttgacagttc ctcagacttt tcttattttt gatgaccttg     900
acagttttga ggagtactgg ttagatatag ggtaatggtt tttaaagtat atttgtcatg     960
atttatactg gggtaagggt ttggggagga agcccatggg gtaaagtact gttctcatca    1020
catcatatca aggttatata ccatcaatat tgccacagat gttacttagc cttttaatat    1080
ttctctaatt tagtgtatat gcaatgatag ttctctgatt tctgagattg agtttctcat    1140
gtgtaatgat tatttagagt ttctctttca tctgttcaaa ttttttgtcta gttttatttt    1200
ttactgattt gtaagacttc tttttataat ctgcatatta caattctctt tactggggtg    1260
ttgcaaatat tttctgtcat tctatggcct gacttttctt aatggttttt taattttaaa    1320
aataagtctt aatattcatg caatctaatt aacaatcttt tctttgtggt taggactttg    1380
agtcataaga aattttttctc tacactgaag tcatgatggc atgcttctat attatttttct   1440
aaaagattta agttttgcc ttctccattt agacttataa ttcactggaa ttttttttgtg    1500
tgtatggtat gacatatggg ttcccttttta ttttttacat ataaatatat ttccctgttt    1560
ttctaaaaaa gaaaagatc atcattttcc cattgtaaaa tgccatattt ttttcatagg    1620
tcacttacat atatcaatgg gtctgtttct gagctctact ctattttatc agcctcactg    1680
tctatcccca cacatctcat gctttgctct aaatcttgat atttagtgga acattctttc    1740
ccattttgtt ctacaagaat attttttgtta ttgtctttgg gctttctata tacatttga    1800
aatgaggttg acaagttaac aaacagcttt tttggggtga acatattgac tacaaattta    1860
tgtgaaaaga aagtatacct tcacaatatt aagtctttta gttcatgaat atagtatgtc    1920
tctccgtttc tgcattaact tagacattca ttaatttctc tcacaattta taagtttatt    1980
tagatcgc                                                              1988
```

<210> SEQ ID NO 5
<211> LENGTH: 858
<212> TYPE: DNA

<213> ORGANISM: Homo sapiens

<400> SEQUENCE: 5

```
cccgggacgg atatcaagca tggggtaaag tactgttctc atcacatcat atcaaggtta    60
tataccatca atattgccac agatgttact tagccttttta atatttctct aatttagtgt  120
atatgcaatg atagttctct gatttctgag attgagtttc tcatgtgtaa tgattattta  180
gagtttctct ttcatctgtt caaattttg tctagttttta ttttttactg atttgtaaga   240
cttcttttta taatctgcat attacaattc tctttactgg ggtgttgcaa atattttctg   300
tcattctatg gcctgacttt tcttaatggt tttttaattt taaaaataag tcttaatatt   360
catgcaatct aattaacaat ctttttctttg tggttaggac tttgagtcat aagaaatttt   420
tctctacact gaagtcatga tggcatgctt ctatattatt ttctaaaaga tttaaagttt   480
tgccttctcc atttagactt ataattcact ggaattttttt tgtgtgtatg gtatgacata  540
tgggttccct tttatttttt acatataaat atatttccct gttttttctaa aaagaaaaa   600
gatcatcatt ttcccattgt aaaatgccat atttttttca taggtcactt acatatatca   660
atgggtctgt ttctgagctc tactctattt tatcagcctc actgtctatc cccacacatc   720
tcatgctttg ctctaaatct tgatatttag tggaacattc tttcccatt tgttctacaa   780
gaatattttt gttattgtct tttgggcttc tatatacatt ttagaatgag gttggcaagt   840
tctgtcagta agtctagc                                                 858
```

<210> SEQ ID NO 6
<211> LENGTH: 170
<212> TYPE: DNA
<213> ORGANISM: Homo sapiens

<400> SEQUENCE: 6

```
taggttacat aatgcttatt gtttcttttc caccattgtc agagttgagt aacaaattct    60
tttttttatt tcttccttttt atttatttat ttatttattt acttatttat ttattttttg  120
agactatcta cgtagcccag cattcaactc tctgcctcac tctgacaaat              170
```

<210> SEQ ID NO 7
<211> LENGTH: 635
<212> TYPE: DNA
<213> ORGANISM: Human immunodeficiency virus type 1

<400> SEQUENCE: 7

```
tggaagggct aattcactcc caaagaagac aagatatcct tgatctgtgg atctaccaca    60
cacaaggcta cttccctgat tagcagaact acacaccagg gccagggggtc agatatccac  120
tgacctttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agacccttttt agtcagtgtg aaaatctct agcag                             635
```

```
<210> SEQ ID NO 8
<211> LENGTH: 291
<212> TYPE: DNA
<213> ORGANISM: Artificial Sequence
<220> FEATURE:
<223> OTHER INFORMATION: Mutated 3' LTR from human immunodeficiency
      virus type 1

<400> SEQUENCE: 8
gaaaagaggg gactggaagg gctaattcac tcccaaagaa gacaagatgc ctcagtgagc     60
gagcgagcgc gcgcgcagag agggagtggc caactcctgc tttttgcctg tactgggtct   120
ctctggttag accagatctg agcctgggag ctctctggct aactagggaa cccactgctt   180
aagcctcaat aaagcttgcc ttgagtgctt caagtagtgt gtgcccgtct gttgtgtgac   240
tctggtaact agagatccct cagacccttt tagtcagtgt ggaaaatctc t             291

<210> SEQ ID NO 9
<211> LENGTH: 125
<212> TYPE: DNA
<213> ORGANISM: adeno-associated virus 2

<400> SEQUENCE: 9
gtgaattacg tcatagggtt agggaggtcc tgtattagag gtcacgtgag tgttttgcga    60
cattttgcga caccatgtgg tcacgctggg tatttaagcc cgagtgagca cgcagggtct   120
ccatt                                                                125

<210> SEQ ID NO 10
<211> LENGTH: 340
<212> TYPE: DNA
<213> ORGANISM: human herpesvirus 5

<400> SEQUENCE: 10
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacccta tgggactttc ctacttggca gtacatctac                          340

<210> SEQ ID NO 11
<211> LENGTH: 95
<212> TYPE: DNA
<213> ORGANISM: Porcine teschovirus-1

<400> SEQUENCE: 11
agggagccac gaacttctct ctgttaaagc aagcaggaga tgttgaagaa aacccgggag    60
cttgtatatc cattttcgga tctcaagaga cagga                               95

<210> SEQ ID NO 12
<211> LENGTH: 17
<212> TYPE: DNA
<213> ORGANISM: Human immunodeficiency virus

<400> SEQUENCE: 12
tggcgcccga acaggga                                                   17

<210> SEQ ID NO 13
<211> LENGTH: 67
```

```
<212> TYPE: DNA
<213> ORGANISM: Human immunodeficiency virus

<400> SEQUENCE: 13
ctcgacgcag gactcggctt gctgaagcgc gcacggcaag aggcgagggg cggcgactgg      60
tgagtac                                                                67

<210> SEQ ID NO 14
<211> LENGTH: 346
<212> TYPE: DNA
<213> ORGANISM: Human immunodeficiency virus

<400> SEQUENCE: 14
tggagaagtg aattatataa atataaagta gtaaaaattg aaccattagg agtagcaccc      60
accaaggcaa agagaagagt ggtgcagaga aaaaaagag cagtgggaat aggagctttg     120
ttccttgggt tcttgggagc agcaggaagc actatgggcg cagcgtcaat gacgctgacg     180
gtacaggcca gacaattatt gtctggtata gtgcagcagc agaacaattt gctgagggct     240
attgaggcgc aacagcatct gttgcaactc acagtctggg gcatcaagca gctccaggca     300
agaatcctgg ctgtggaaag atacctaaag gatcaacagc tcctgg                    346

<210> SEQ ID NO 15
<211> LENGTH: 124
<212> TYPE: DNA
<213> ORGANISM: Human immunodeficiency virus

<400> SEQUENCE: 15
tttaaaagaa aaggggggat tggggggtac agtgcagggg aaagaatagt agacataata      60
gcaacagaca tacaaactaa agaactacaa aaacaaatta caaaaattca aaattttcgg     120
gttt                                                                  124

<210> SEQ ID NO 16
<211> LENGTH: 671
<212> TYPE: DNA
<213> ORGANISM: Escherichia coli

<400> SEQUENCE: 16
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata aagataccag gcgtttcccc ctggaagctc cctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag aacagtattt ggtatctgcg ctctgctgaa gccagttacc     540
ttcggaaaaa gagttggtag ctcttgatcc ggcaaacaaa ccaccgctgg tagcggtttt     600
tttgtttgca gcagcagat tacgcgcaga aaaaaaggat ctcaagaaga tcctttgatc     660
ttttctacgg g                                                          671

<210> SEQ ID NO 17
<211> LENGTH: 288
<212> TYPE: PRT
```

<213> ORGANISM: Human immunodeficiency virus

<400> SEQUENCE: 17

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Val
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Gly Ala Thr Val Arg Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 18
<211> LENGTH: 20
<212> TYPE: DNA
<213> ORGANISM: Artificial Sequence
<220> FEATURE:
<223> OTHER INFORMATION: qLTR Fw oligonucleotide primer

<400> SEQUENCE: 18
tgtgtgcccg tctgttgtgt                                                20

<210> SEQ ID NO 19
<211> LENGTH: 20
<212> TYPE: DNA
<213> ORGANISM: Artificial Sequence
<220> FEATURE:
<223> OTHER INFORMATION: qLTR Rv oligonucleotide Primer

<400> SEQUENCE: 19

```
gagtcctgcg tcgagagagc                                              20

<210> SEQ ID NO 20
<211> LENGTH: 22
<212> TYPE: DNA
<213> ORGANISM: Artificial Sequence
<220> FEATURE:
<223> OTHER INFORMATION: qhAlb Fw oligonucleotide Primer

<400> SEQUENCE: 20
gctgtcatct cttgtgggct gt                                           22

<210> SEQ ID NO 21
<211> LENGTH: 21
<212> TYPE: DNA
<213> ORGANISM: Artificial Sequence
<220> FEATURE:
<223> OTHER INFORMATION: qhAlb Rv oligonucleotide primer

<400> SEQUENCE: 21
actcatggga gctgctggtt c                                            21

<210> SEQ ID NO 22
<211> LENGTH: 25
<212> TYPE: DNA
<213> ORGANISM: Artificial Sequence
<220> FEATURE:
<223> OTHER INFORMATION: q2LTR R Rv2 oligonucleotide primer

<400> SEQUENCE: 22
tgaagcactc aaggcaagct ttatt                                        25

<210> SEQ ID NO 23
<211> LENGTH: 25
<212> TYPE: DNA
<213> ORGANISM: Artificial Sequence
<220> FEATURE:
<223> OTHER INFORMATION: q2LTR U5 Fw2 oligonucleotide primer

<400> SEQUENCE: 23
gtgtgtgccc gtctgttgtg tgact                                        25

<210> SEQ ID NO 24
<211> LENGTH: 8310
<212> TYPE: DNA
<213> ORGANISM: Artificial Sequence
<220> FEATURE:
<223> OTHER INFORMATION: pLS1 plasmid

<400> SEQUENCE: 24
ctttaagacc aatgacttac aaggcagctg tagatcttag ccactttta aaagaaaaga     60 ggggactgga agggctaatt cactcccaaa gaagacaaga tgcctcagtg agcgagcgag   120
cgcgcgcgca gagagggagt ggccaactcc tgcttttgc ctgtactggg tctctctggt   180
tagaccagat ctgagcctgg gagctctctg gctaactagg gaacccactg cttaagcctc   240
aataaagctt gccttgagtg cttcaagtag tgtgtgcccg tctgttgtgt gactctggta   300
actagagatc cctcagaccc ttttagtcag tgtggaaaat ctctagcagc tagcgtttta   360
ccgtcgacct ctagctagag cttggcgtaa tcatggtcat agctgtttcc tgtgtgaaat   420
tgttatccgc tcacaattcc acacaacata cgagccggaa gcataaagtg taaagcctgg   480
ggtgcctaat gagtgagcta actcacatta attgcgttgc gctcactgcc cgctttccag   540
```

-continued

```
tcgggaaacc tgtcgtgcca gctgcattaa tgaatcggcc aacgcgcggg gagaggcggt      600
ttgcgtattg ggcgctcttc cgcttcctcg ctcactgact cgctgcgctc ggtcgttcgg      660
ctgcggcgag cggtatcagc tcactcaaag gcggtaatac ggttatccac agaatcaggg     720
gataacgcag gaaagaacat gtgagcaaaa ggccagcaaa aggccaggaa ccgtaaaaag     780
gccgcgttgc tggcgttttt ccataggctc cgcccccctg acgagcatca caaaaatcga     840
cgctcaagtc agaggtggcg aaacccgaca ggactataaa gataccaggc gtttccccct     900
ggaagctccc tcgtgcgctc tcctgttccg accctgccgc ttaccggata cctgtccgcc     960
tttctccctt cgggaagcgt ggcgctttct catagctcac gctgtaggta tctcagttcg    1020
gtgtaggtcg ttcgctccaa gctgggctgt gtgcacgaac cccccgttca gcccgaccgc    1080
tgcgccttat ccggtaacta tcgtcttgag tccaacccgg taagacacga cttatcgcca    1140
ctggcagcag ccactggtaa caggattagc agagcgaggt atgtaggcgg tgctacagag    1200
ttcttgaagt ggtggcctaa ctacggctac actagaagaa cagtatttgg tatctgcgct    1260
ctgctgaagc cagttacctt cggaaaaaga gttggtagct cttgatccgg caaacaaacc    1320
accgctggta gcggtttttt tgtttgcaag cagcagatta cgcgcagaaa aaaggatct     1380 caagaagatc ctttgatctt ttctacgggg tctgacgctc agtggaacga aaactcacgt    1440
taagggattt tggtcatgag attatcaaaa aggatcttca cctagatcct tttaaattaa    1500
aaatgaagtt ttaaatcaat ctaaagtata tatgagtaaa cttggtctga cagttaccaa    1560
tgcttaatca gtgaggcacc tatctcagcg atctgtctat ttcgttcatc catagttgcc    1620
tgactccccg tcgtgtagat aactacgata cgggagggct taccatctgg ccccagtgct    1680
gcaatgatac cgcgagaccc acgctcaccg gctccagatt tatcagcaat aaaccagcca    1740
gccgaagggg ccgagcgcag aagtggtcct gcaactttat ccgcctccat ccagtctatt    1800
aattgttgcc gggaagctag agtaagtagt tcgccagtta atagtttgcg caacgttgtt    1860
gccattgcta caggcatcgt ggtgtcacgc tcgtcgtttg gtatggcttc attcagctcc    1920
ggttcccaac gatcaaggcg agttacatga tcccccatgt tgtgcaaaaa agcggttagc    1980
tccttcggtc ctccgatcgt tgtcagaagt aagttggccg cagtgttatc actcatggtt    2040
atggcagcac tgcataattc tcttactgtc atgccatccg taagatgctt ttctgtgact    2100
ggtgagtact caaccaagtc attctgagaa tagtgtatgc ggcgaccgag ttgctcttgc    2160
ccggcgtcaa tacgggataa taccgcgcca catagcagaa ctttaaaagt gctcatcatt    2220
ggaaaacgtt cttcggggcg aaaactctca aggatcttac cgctgttgag atccagttcg    2280
atgtaaccca ctcgtgcacc caactgatct tcagcatctt ttactttcac cagcgtttct    2340
gggtgagcaa aaacaggaag gcaaaatgcc gcaaaaaagg gaataagggc gacacggaaa    2400
tgttgaatac tcatactctt cctttttcaa tattattgaa gcatttatca gggttattgt    2460
ctcatgagcg gatacatatt tgaatgtatt tagaaaaata aacaaatagg ggttccgcgc    2520
acatttcccc gaaaagtgcc acctgacgtc gacggatcgg gagatcaact tgtttattgc    2580
agcttataat ggttacaaat aaagcaatag catcacaaat ttcacaaata agcatttttt    2640
ttcactgcat tctagttgtg gtttgtccaa actcatcaat gtatcttatc atgtctggat    2700
caactggata actcaagcta accaaaatca tcccaaactt cccaccccat acctattac     2760 cactgccaat acctagtgg tttcatttac tctaaacctg tgattcctct gaattatttt     2820
cattttaaag aaattgtatt tgttaaatat gtactacaaa cttagtagtt tttaagaaa     2880 ttgtatttgt taaatatgta ctacaaactt agtagttgga agggctaatt cactcccaaa    2940
```

```
gaagacaaga tatccttgat ctgtggatct accacacaca aggctacttc cctgattagc    3000
agaactacac accagggcca ggggtcagat atccactgac ctttggatgg tgctacaagc    3060
tagtaccagt tgagccagat aaggtagaag aggccaataa aggagagaac accagcttgt    3120
tacaccctgt gagcctgcat gggatggatg acccggagag agaagtgtta gagtggaggt    3180
ttgacagccg cctagcattt catcacgtgg cccgagagct gcatccggag tacttcaaga    3240
actgctgata tcgagcttgc tacaagggac tttccgctgg ggactttcca gggaggcgtg    3300
gcctgggcgg gactggggag tggcgagccc tcagatcctg catataagca gctgcttttt    3360
gcctgtactg ggtctctctg gttagaccag atctgagcct gggagctctc tggctaacta    3420
gggaacccac tgcttaagcc tcaataaagc ttgccttgag tgcttcaagt agtgtgtgcc    3480
cgtctgttgt gtgactctgg taactagaga tccctcagac ccttttagtc agtgtggaaa    3540
atctctagca gtggcgcccg aacagggact tgaaagcgaa agggaaacca gaggagctct    3600
ctcgacgcag gactcggctt gctgaagcgc gcacggcaag aggcgagggg cggcgactgg    3660
tgagtacgcc aaaaattttg actagcggag gctagaagga gagagatggg tgcgagagcg    3720
tcagtattaa gcgggggaga attagatcgc gatgggaaaa aattcggtta aggccagggg    3780
gaaagaaaaa atataaatta aaacatatag tatgggcaag cagggagcta gaacgattcg    3840
cagttaatcc tggcctgtta gaaacatcag aaggctgtag acaaatactg ggacagctac    3900
aaccatccct tcagacagga tcagaagaac ttagatcatt atataataca gtagcaaccc    3960
tctattgtgt gcatcaaagg atagagataa aagacaccaa ggaagcttta gacaagatag    4020
aggaagagca aaacaaaagt aagaccaccg cacagcaagc ggccggccgc tgatcttcag    4080
acctggagga ggagatatga gggacaattg gagaagtgaa ttatataaat ataaagtagt    4140
aaaaattgaa ccattaggag tagcacccac caaggcaaag agaagagtgg tgcagagaga    4200
aaaaagagca gtgggaatag gagctttgtt ccttgggttc ttgggagcag caggaagcac    4260
tatgggcgca gcgtcaatga cgctgacggt acaggccaga caattattgt ctggtatagt    4320
gcagcagcag aacaatttgc tgagggctat tgaggcgcaa cagcatctgt tgcaactcac    4380
agtctggggc atcaagcagc tccaggcaag aatcctggct gtggaaagat acctaaagga    4440
tcaacagctc ctggggattt ggggttgctc tggaaaactc atttgcacca ctgctgtgcc    4500
ttggaatgct agttggagta ataaatctct ggaacagatt tggaatcaca cgacctggat    4560
ggagtgggac agagaaatta acaattacac aagcttaata cactccttaa ttgaagaatc    4620
gcaaaaccag caagaaaaga atgaacaaga attattggaa ttagataaat gggcaagttt    4680
gtggaattgg tttaacataa caaattggct gtggtatata aaattattca taatgatagt    4740
aggaggcttg gtaggtttaa gaatagtttt tgctgtactt tctatagtga atagagttag    4800
gcagggatat tcaccattat cgtttcagac ccacctccca accccgaggg gacccgacag    4860
gcccgaagga atagaagaag aaggtggaga gagagacaga gacagatcca ttcgattagt    4920
gaacggatct cgacggtatc gcctttaaaa gaaaggggg gattgggggg tacagtgcag    4980
gggaaagaat agtagacata atagcaacag acatacaaac taaagaacta caaaaacaaa    5040
ttacaaaaat tcaaaatttt cgggtttatt acagggacag cagagatcca gtttatcgaa    5100
ttctagttat taatagtaat caattacggg gtcattagtt catagcccat atatggagtt    5160
ccgcgttaca taacttacgg taaatggccc gcctggctga ccgcccaacg acccccgccc    5220
attgacgtca ataatgacgt atgttcccat agtaacgcca tagggacttt ccattgacg    5280
```

```
tcaatgggtg gagtatttac ggtaaactgc ccacttggca gtacatcaag tgtatcatat    5340
gccaagtacg cccctattg acgtcaatga cggtaaatgg cccgcctggc attatgccca     5400
gtacatgacc ttatgggact ttcctacttg gcagtacatc tacgtgaatt acgtcatagg    5460
gttagggagg tcctgtatta gaggtcacgt gagtgttttg cgacattttg cgacaccatg    5520
tggtcacgct gggtatttaa gcccgagtga gcacgcaggg tctccattag cgcttccgga    5580
actagtggat ccaccggtcg ccaccatggt gagcaagggc gaggagctgt tcaccggggt    5640
ggtgcccatc ctggtcgagc tggacggcga cgtaaacggc cacaagttca gcgtgtccgg    5700
cgagggcgag ggcgatgcca cctacggcaa gctgaccctg aagttcatct gcaccaccgg    5760
caagctgccc gtgccctggc ccacccctcgt gaccaccctg acctacggcg tgcagtgctt    5820
cagccgctac cccgaccaca tgaagcagca cgacttcttc aagtccgcca tgcccgaagg    5880
ctacgtccag gagcgcacca tcttcttcaa ggacgacggc aactacaaga cccgcgccga    5940
ggtgaagttc gagggcgaca ccctgggtga accgcatcga gctgaagggc atcgacttca    6000
aggaggcggc aacatcctgg ggcacaagct ggagtacaac tacaacagcc acaacgtcta    6060
tatcatggcc gacaagcaga agaacggcat caaggtgaac ttcaagatcc gccacaacat    6120
cgaggacggc agcgtgcagc tcgccgacca ctaccagcag aacacccca tcggcgacgg    6180
ccccgtgctg ctgccgaca accactacct gagcacccag tccgccctga gcaaagaccc    6240
caacgagaag cgcgatcaca tggtcctgct ggagttcgtg accgccgccg ggatcactct    6300
cggcatggac gagctgtaca agggagccac gaacttctct ctgttaaagc aagcaggaga    6360
tgttgaagaa aacccgggag cttgtatatc cattttcgga tctcaagaga caggaattga    6420
acaagatgga ttgcacgcag gttctccggc cgcttgggtg gagaggctat tcggctatga    6480
ctgggcacaa cagacaatcg gctgctctga tgccgccgtg ttccggctgt cagcgcaggg    6540
gcgcccggtt ctttttgtca agaccgacct gtccggtgcc ctgaatgaac tgcaggacga    6600
ggcagcgcgc tatcgtggc tggccacgac gggcgttcct tgcgcagctg tgctcgacgt    6660
tgtcactgaa gcgggaaggg actggctgct attgggcgaa gtgccggggc aggatctcct    6720
gtcatctcac cttgctcctg ccgagaaagt atccatcatg gctgatgcaa tgcggcggct    6780
gcatacgctt gatccggcta cctgcccatt cgaccaccaa gcgaaacatc gcatcgagcg    6840
agcacgtact cggatggaag ccggtcttgt cgatcaggat gatctggacg aagagcatca    6900
ggggctcgcg ccagccgaac tgttcgccag gctcaaggcg cgcatgcccg acggcgagga    6960
tctcgtcgtg acccatggcg atgcctgctt gccgaatatc atggtggaaa atggccgctt    7020
ttctggattc atcgactgtg gccggctggg tgtggcggac cgctatcagg acatagcgtt    7080
ggctacccgt gatattgctg aagagcttgg cggcgaatgg gctgaccgct tcctcgtgct    7140
ttacggtatc gccgctcccg attcgcagcg catcgccttc tatcgccttc ttgacgagtt    7200
cttctgagcg ggactctggg gttcgaatag gttacataat gcttattgtt tctttccac    7260
cattgtcaga gttgagtaac aaattctttt ttttatttct tccttttatt tatttattta    7320
tttatttact tatttatttta tttttgaga ctatctacgt agcccagcat tcaactctct    7380
gcctcactct gacaaatctc gagtctgat gctggaggtc gaccagatgt ccgaaagtgt    7440
cccccccccc ccccccccc ggcgcggagc ggcggggcca ctctctagag aattctggct    7500
gccttccagg cattaatttc ctagttcact gactcacaat ttttctgaa tactagtgaa    7560
agtgcactgt atgtaacccg caaacgtgta ttcacatttt atttacgctt cgactcagct    7620
agttgcccag ccccacacat gatttgtttg ctccctgaaa tgatctatat ttaatatata    7680
```

```
atgtatattc cctcgggatt ttttattttg tgttattcca cggcatgaaa aacaaaaaac    7740
attcttctca tccttggtcc ctcacccaaa ggcattttaa gtaaactttt ctctccctcc    7800
accacctcca aaagagaaaa caattcgggg gaaaggggtg tgtgtatagc atgtacgctg    7860
ttcaagatgg gttattaccc gttgagtttg cagctcagcg ttcaagtgtt aagtgaatat    7920
agtagcttcc aaatccgatg cactgcacaa ttcagcttta aggattgcaa attactcctg    7980
cctccaggcc tttgccgcaa acgcggggag caaccaatcg ctatgctgga ttttgctgca    8040
aagcgtcttt ccctccgccc cctctctggg cagcacccgc gttcaggttt gcgaaagtaa    8100
agtaagtgtg ccctctactg gcagcagaga tcatcgcgcc tggatgtcaa cgagggcggg    8160
ggtcaggtgg gggcaggagc aggagcgtcc gaggtgcaag gtttccagcg ggggaaggac    8220
aggcggttcc ttaaaacaag tttccagcca cctccttgtt attctttcag gttggctgca    8280
gaaggtccga agaaagagga gttacggtac                                     8310

<210> SEQ ID NO 25
<211> LENGTH: 36
<212> TYPE: DNA
<213> ORGANISM: Artificial Sequence
<220> FEATURE:
<223> OTHER INFORMATION: S/MAR Consensus Sequence

<400> SEQUENCE: 25
cctmdawksg bytsmaawtw bcmyttrsca aattcc                              36
```